(12) United States Patent
Jo et al.

(10) Patent No.: US 10,702,190 B2
(45) Date of Patent: Jul. 7, 2020

(54) METHOD FOR RECOGNIZING USER ACTIVITY AND ELECTRONIC DEVICE FOR THE SAME

(71) Applicant: Samsung Electronics Co., Ltd., Gyeonggi-do (KR)

(72) Inventors: Yanggu Jo, Seoul (KR); Seungbeom Ryu, Gyeonggi-do (KR); Byungjun Lee, Gyeonggi-do (KR); Wonhee Lee, Gyeonggi-do (KR); Jeong Gwan Kang, Gyeonggi-do (KR); Taeho Kim, Chungcheongbuk-do (KR); Jeong-Min Park, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 211 days.

(21) Appl. No.: 15/800,348

(22) Filed: Nov. 1, 2017

(65) Prior Publication Data

US 2018/0116561 A1 May 3, 2018

(30) Foreign Application Priority Data

Nov. 1, 2016 (KR) .................. 10-2016-0144215

(51) Int. Cl.
*A61B 5/11* (2006.01)
*G16H 40/60* (2018.01)
(Continued)

(52) U.S. Cl.
CPC .......... *A61B 5/1123* (2013.01); *A61B 5/4806* (2013.01); *A61B 5/7225* (2013.01);
(Continued)

(58) Field of Classification Search
None
See application file for complete search history.

(56) References Cited

U.S. PATENT DOCUMENTS 7,813,892 B2 10/2010 Sugawara et al.
8,543,185 B2 9/2013 Yuen et al.
(Continued)

FOREIGN PATENT DOCUMENTS

KR 10-2015-0132595 A 11/2015

OTHER PUBLICATIONS

European Search Report dated Mar. 21, 2018.
European Search Report dated Jan. 14, 2020.

*Primary Examiner* — Kennedy Schaetzle
(74) *Attorney, Agent, or Firm* — Cha & Reiter, LLC

(57) ABSTRACT

Various exemplary embodiments provide an electronic device configured to include one or more sensor modules, at least one memory, a display, and a first processor or second processor operatively coupled to the one or more sensor modules, the at least one memory, and/or the display, wherein the first processor is configured to acquire sensor data from at least one sensor module among the one or more sensor modules, calculate a difference between at least two data points in the acquired sensor data, determine user's activity information based on at least one of a period of the sensor data, a magnitude of the difference, and a change amount of the difference, and deliver the user's activity information to the second processor, and wherein the second processor is configured to display, on the display, a user interface related to the user's activity information delivered from the first processor. Other exemplary embodiments are also possible.

19 Claims, 12 Drawing Sheets

(51) Int. Cl.
*G16H 20/30* (2018.01)
*A61B 5/00* (2006.01)
*G08B 13/14* (2006.01)
*G08B 21/04* (2006.01)

(52) U.S. Cl.
CPC .......... *A61B 5/742* (2013.01); *G08B 13/1436* (2013.01); *G16H 20/30* (2018.01); *G16H 40/60* (2018.01); *A61B 5/7264* (2013.01); *A61B 2562/0219* (2013.01); *G08B 21/0453* (2013.01)

(56) References Cited

U.S. PATENT DOCUMENTS

| | | | |
|---|---|---|---|
| 2010/0305480 | A1 | 12/2010 | Fu et al. |
| 2013/0138171 | A1* | 5/2013 | Wahlberg ........... A61N 1/36514 607/19 |
| 2014/0052010 | A1* | 2/2014 | Kasama ................ A61B 5/024 600/508 |
| 2015/0119728 | A1 | 4/2015 | Blackadar et al. |
| 2016/0000359 | A1 | 1/2016 | Li et al. |
| 2016/0034634 | A9 | 2/2016 | Hong et al. |
| 2016/0144235 | A1 | 5/2016 | Martikka et al. |
| 2016/0337843 | A1* | 11/2016 | Repka ..................... H04W 8/22 |
| 2017/0128020 | A1* | 5/2017 | Olivier ................. A61B 5/0022 |
| 2017/0164851 | A1* | 6/2017 | Takahashi .......... A61B 5/02438 |

\* cited by examiner

METHOD FOR RECOGNIZING USER ACTIVITY AND ELECTRONIC DEVICE FOR THE SAME

CLAIM OF PRIORITY

This application claims priority under 35 U.S.C. § 119(a) to Korean Patent Application Serial No. 10-2016-0144215, which was filed in the Korean Intellectual Property Office on Nov. 1, 2016, the content of which is incorporated herein by reference.

BACKGROUND

1. Field of the Disclosure

Various exemplary embodiments in the present disclosure generally relate to a method and apparatus for recognizing a user activity.

2. Description of the Related Art

Recently, as the development of digital technologies have advanced, use of various types of electronic devices such as mobile communication terminals, Personal Digital Assistants (PDA), electronic organizers, smart phones, tablet Personal Computers (PCs), wearable devices, or the like have increased. These electronic devices may support various functions.

For instance, an electronic device may include at least one sensor, and may collect information regarding the state of the electronic device and activity information of the user using sensor data acquired from the sensor. In one example, the sensor may be an acceleration sensor, and it may be used to determine that the electronic device is moving at such a speed that the electronic device may itself to be in a moving vehicle, and change into a drive mode. Alternatively, when the electronic device uses the acceleration sensor to determine that the user is walking or running, health information such as the number of steps or a running time or the like may be collected to provide a health service.

Electronic devices may utilize various sensors included therein to provide health services to the user. For example, an electronic device may use a heart rate sensor to measure the user's heart rate and provide various health-related information based on the measured heart rate. However, the heart rate sensor consumes a great amount of power. In addition, electronic devices may use acceleration sensors to measure the number of steps and provide a variety of information related to exercise based on the measured number of steps. However, exercises not related to the number of steps (such as strength training) may not be recognized as exercise. Further, the electronic device may provide information related to exercise when a specific regular pattern, such as one generated when walking, is detected. However, exercises with irregular patterns may not be recognized as an exercise.

SUMMARY

According to one exemplary embodiment, an electronic device may include one or more sensor modules, at least one memory, a display, and a first processor or second processor operatively coupled to the one or more sensor modules, the at least one memory, and/or the display. The first processor may be configured to acquire sensor data from at least one sensor module among the one or more sensor modules, calculate a difference between at least two data points in the acquired sensor data, determine user's activity information based on at least one of a period of the sensor data, a magnitude of the difference, and a change amount of the difference, and deliver the user's activity information to the second processor. The second processor may be configured to display, on the display, a user interface related to the user's activity information delivered from the first processor.

According to one exemplary embodiment, a method of operating an electronic device including one or more sensor modules may include acquiring sensor data from at least one sensor module among the one or more sensor modules, calculating a difference between at least two data points in the acquired sensor data, determining user's activity information based on at least one of a period of the sensor data, a magnitude of the difference, and a change amount of the difference, and displaying a user interface related to the user's activity information.

According to one exemplary embodiment, the user's activity in which the movement pattern is irregular may be recognized as an activity exercise by using sensor data, and a user interface related to the activity exercise may be provided.

According to one exemplary embodiment, if sensor data greater than or equal to a specific intensity is continuously detected, even if the movement is not regular, a user activity exercise may be recognized. Therefore, the present disclosure describes an advantage over the prior art where irregular exercise may be detected.

According to one exemplary embodiment, if a period of sensor data is irregular, and if a change in the difference in the sensor data is continuous, and if high-intensity movement is detected, then irregular exercise may be detected.

According to one exemplary embodiment, since repetitive and regular movement may be detected by using a sensor with relatively low power consumption, other sensors, which may be used to more accurately determining the type of regular exercise, may be activated only when the repetitive and regular movement is detected.

DETAILED DESCRIPTION

Figure 1:
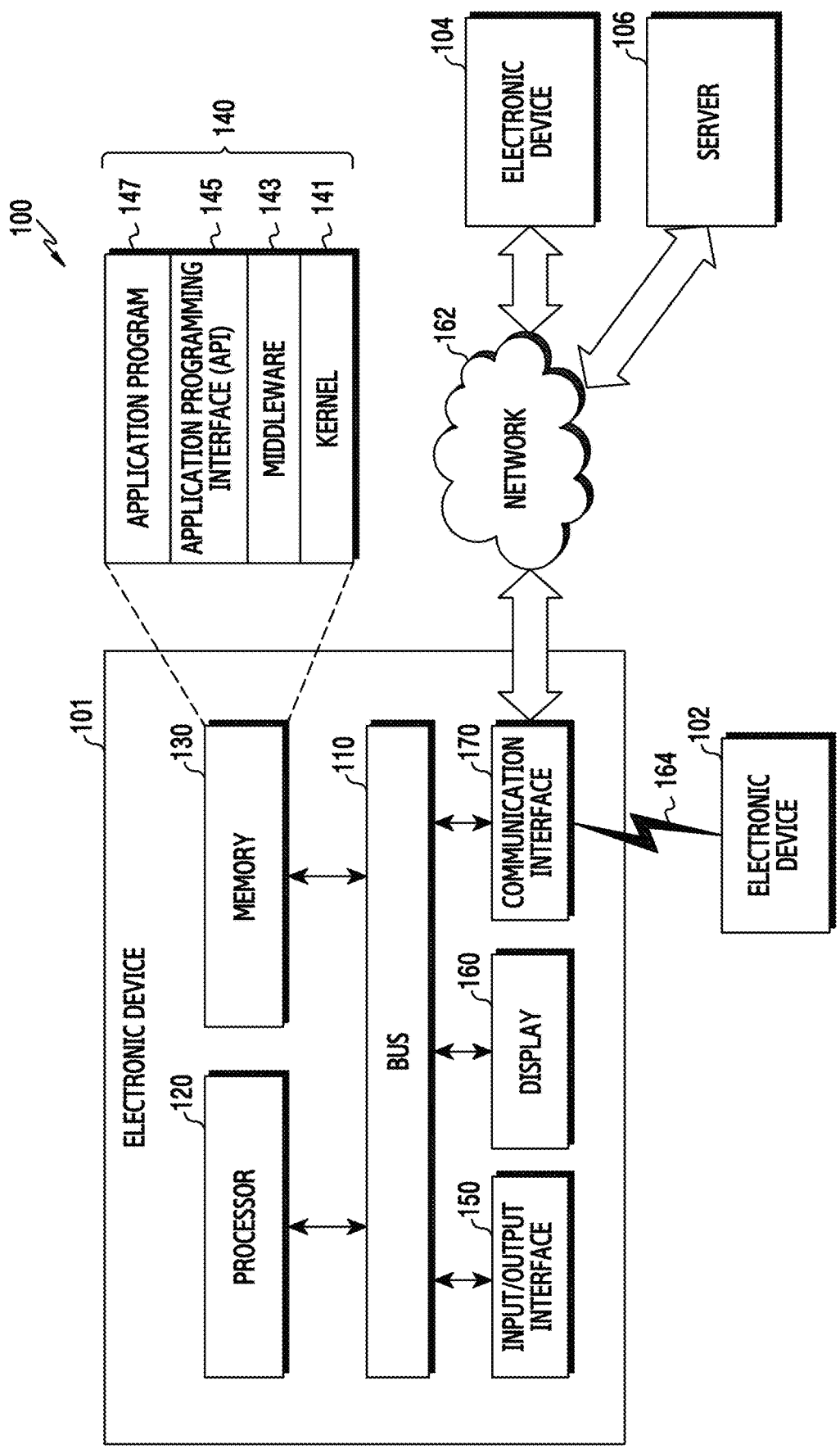
FIG. 1 is a block diagram illustrating an electronic device in a network environment according to one exemplary embodiment.

Hereinafter, various embodiments of the present disclosure will be described with reference to the accompanying drawings. However, it should be understood that there is no intent to limit the present disclosure to the particular forms disclosed herein; rather, the present disclosure should be construed to cover various modifications, equivalents, and/or alternatives of embodiments of the present disclosure. In describing the drawings, similar reference numerals may be used to designate similar constituent elements. As used herein, the expression "have," "may have," "include," or "may include" refers to the existence of a corresponding feature (e.g., numeral, function, operation, or constituent element such as component), and does not exclude one or more additional features. In the present disclosure, the expression "A or B," "at least one of A or/and B," or "one or more of A or/and B" may include all possible combinations of the items listed. For example, the expression "A or B," "at least one of A and B," or "at least one of A or B" refers to all of (1) including at least one A, (2) including at least one B, or (3) including all of at least one A and at least one B. The expression "a first," "a second," "the first," or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposer between them. In contrast, it may be understood that when an element (e.g., first element) is referred to as being "directly connected," or "directly coupled" to another element (second element), there are no element (e.g., third element) interposed between them.

The expression "configured to" used in the present disclosure may be exchanged with, for example, "suitable for," "having the capacity to," "designed to," "adapted to," "made to," or "capable of" according to the situation. The term "configured to" may not necessarily imply "specifically designed to" in hardware. Alternatively, in some situations, the expression "device configured to" may mean that the device, together with other devices or components, "is able to." For example, the phrase "processor adapted (or configured) to perform A, B, and C" may mean a dedicated processor (e.g. embedded processor) only for performing the corresponding operations or a generic-purpose processor (e.g., central processing unit (CPU) or application processor (AP)) that can perform the corresponding operations by executing one or more software programs stored in a memory device.

The terms used in the present disclosure are only used to describe specific embodiments, and are not intended to limit the present disclosure. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have excessively formal or narrow meanings unless clearly defined in the present disclosure. In some cases, even the term explicitly defined in the present disclosure should not be interpreted to exclude embodiments of the present disclosure.

An electronic device according to various embodiments of the present disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device. According to various embodiments, the wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit). According to some embodiments, the electronic device may be a home appliance. The home appliance may include at least one of, for example, a television, a Digital Video Disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

According to another embodiment, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, etc.).

According to some embodiments, the electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device according to various embodiments of the present disclosure may be a combination of one or more of the aforementioned various devices. The electronic device according to some embodiments of the present disclosure may be a flexible device. Further, the electronic device according to an embodiment of the present disclosure is not limited to the aforementioned devices, and may include a new electronic device according to the development of technology. Hereinafter, an electronic device according to various embodiments will be described with reference to the accompanying drawings. As used herein, the term "user" may indicate a person who uses an electronic device or a device (e.g., an artificial intelligence electronic device) that uses an electronic device.

FIG. 1 is a block diagram illustrating a network environment including an electronic device according to one embodiment of the present disclosure.

An electronic device 101 within a network environment 100, according to various embodiments, will be described with reference to FIG. 1. The electronic device 101 may include a bus 110, a processor 120, a memory 130, an input/output interface 150, a display 160, and a communication interface 170. According to an embodiment of the present disclosure, the electronic device 101 may omit at least one of the above components or may further include other components.

The bus 110 may include, for example, a circuit which interconnects the components 110 to 170 and delivers a communication (e.g., a control message and/or data) between the components 110 to 170.

The processor 120 may include one or more of a Central Processing Unit (CPU), an Application Processor (AP), and a Communication Processor (CP). The processor 120 may carry out, for example, calculation or data processing relating to control and/or communication of at least one other component of the electronic device 101. The processor 120 may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

The memory 130 may include a volatile memory and/or a non-volatile memory. The memory 130 may store, for example, commands or data relevant to at least one other component of the electronic device 101. According to an embodiment of the present disclosure, the memory 130 may store software and/or a program 140. The program 140 may include, for example, a kernel 141, middleware 143, an Application Programming Interface (API) 145, and/or application programs (or "applications") 147. At least some of the kernel 141, the middleware 143, and the API 145 may be referred to as an Operating System (OS).

The kernel 141 may control or manage system resources (e.g., the bus 110, the processor 120, or the memory 130) used for performing an operation or function implemented in the other programs (e.g., the middleware 143, the API 145, or the application programs 147). Furthermore, the kernel 141 may provide an interface through which the middleware 143, the API 145, or the application programs 147 may access the individual components of the electronic device 101 to control or manage the system resources.

The middleware 143, for example, may serve as an intermediary for allowing the API 145 or the application programs 147 to communicate with the kernel 141 to exchange data. Also, the middleware 143 may process one or more task requests received from the application programs 147 according to priorities thereof. For example, the middleware 143 may assign priorities for using the system resources (e.g., the bus 110, the processor 120, the memory 130, or the like) of the electronic device 101, to at least one of the application programs 147. For example, the middleware 143 may perform scheduling or loading balancing on the one or more task requests by processing the one or more task requests according to the priorities assigned thereto.

The API 145 is an interface through which the applications 147 control functions provided from the kernel 141 or the middleware 143, and may include, for example, at least one interface or function (e.g., instruction) for file control, window control, image processing, character control, and the like.

The input/output interface 150, for example, may function as an interface that may transfer commands or data input from a user or another external device to the other element(s) of the electronic device 101. Furthermore, the input/output interface 150 may output the commands or data received from the other element(s) of the electronic device 101 to the user or another external device.

Examples of the display 160 may include a Liquid Crystal Display (LCD), a Light-Emitting Diode (LED) display, an Organic Light-Emitting Diode (OLED) display, a MicroElectroMechanical Systems (MEMS) display, and an electronic paper display. The display 160 may display, for example, various types of contents (e.g., text, images, videos, icons, or symbols) to users. The display 160 may include a touch screen, and may receive, for example, a touch, gesture, proximity, or hovering input using an electronic pen or a user's body part.

The communication interface 170 may establish communication, for example, between the electronic device 101 and an external device (e.g., a first external electronic device 102, a second external electronic device 104, or a server 106). For example, the communication interface 170 may be connected to a network 162 through wireless or wired communication, and may communicate with an external device (e.g., the second external electronic device 104 or the server 106). The wireless communication may use at least one of, for example, Long Term Evolution (LTE), LTE-Advance (LTE-A), Code Division Multiple Access (CDMA), Wideband CDMA (WCDMA), Universal Mobile Telecommunications System (UMTS), Wireless Broadband (WiBro), and Global System for Mobile Communications (GSM), as a cellular communication protocol. In addition, the wireless communication may include, for example, short range communication 164.

The short-range communication 164 may include at least one of, for example, Wi-Fi, Bluetooth, Near Field Communication (NFC), and Global Navigation Satellite System (GNSS). GNSS may include, for example, at least one of global positioning system (GPS), global navigation satellite system (Glonass), Beidou Navigation satellite system (Beidou) or Galileo, and the European global satellite-based navigation system, based on a location, a bandwidth, or the like. Hereinafter, in the present disclosure, the "GPS" may be interchangeably used with the "GNSS". The wired communication may include, for example, at least one of a Universal Serial Bus (USB), a High Definition Multimedia Interface (HDMI), Recommended Standard 232 (RS-232), and a Plain Old Telephone Service (POTS). The network 162 may include at least one of a telecommunication network such as a computer network (e.g., a LAN or a WAN), the Internet, and a telephone network.

Each of the first and second external electronic devices 102 and 104 may be of a type identical to or different from that of the electronic device 101. According to an embodiment of the present disclosure, the server 106 may include a group of one or more servers. According to various embodiments of the present disclosure, all or some of the operations performed in the electronic device 101 may be executed in another electronic device or a plurality of electronic devices (e.g., the electronic devices 102 and 104 or the server 106). According to an embodiment of the present disclosure, when the electronic device 101 has to perform some functions or services automatically or in response to a request, the electronic device 101 may request another device (e.g., the electronic device 102 or 104 or the server 106) to execute at least some functions relating thereto instead of or in addition to autonomously performing the functions or services. Another electronic device (e.g., the electronic device 102 or 104, or the server 106) may execute the requested functions or the additional functions, and may deliver a result of the execution to the electronic device 101. The electronic device 101 may process the received result as it is or additionally, and may provide the requested functions or services. To this end, for example, cloud computing, distributed computing, or client-server computing technologies may be used.

Figure 2:
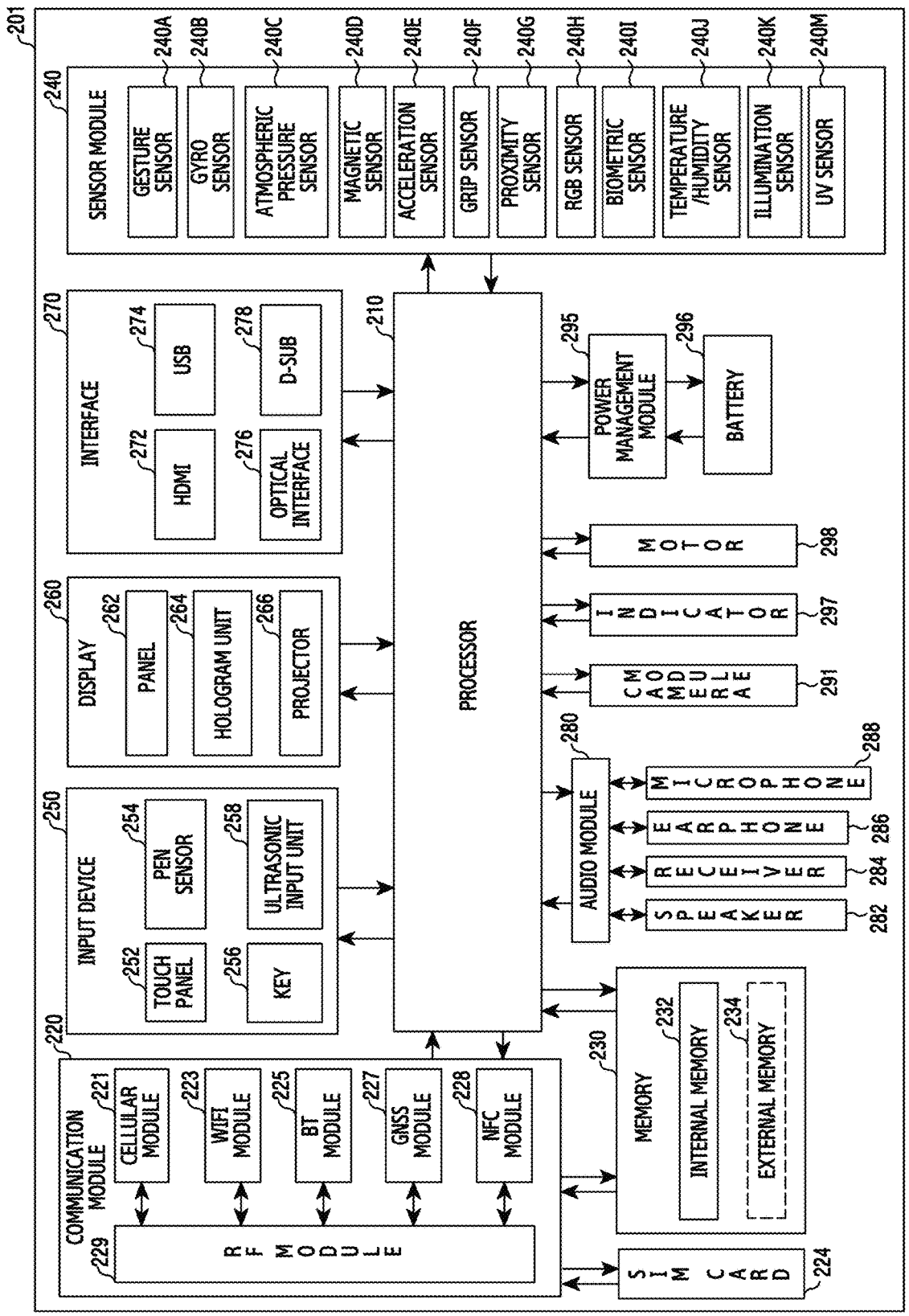
FIG. 2 is a block diagram illustrating structures of an electronic device according to one exemplary embodiment.

FIG. 2 is a block diagram of an electronic device according to one embodiment of the present disclosure.

The electronic device 201 may include, for example, all or a part of the electronic device 101 shown in FIG. 1. The electronic device 201 may include one or more processors 210 (e.g., Application Processors (AP)), a communication module 220, a memory 230, a sensor module 240, an input device 250, a display 260, an interface 270, an audio module 280, a camera module 291, a power management module 295, a battery 296, an indicator 297, and a motor 298.

The processor 210 may control a plurality of hardware or software components connected to the processor 210 by driving an operating system or an application program, and perform processing of various pieces of data and calculations. The processor 210 may be embodied as, for example, a System on Chip (SoC). According to an embodiment of the present disclosure, the processor 210 may further include a Graphic Processing Unit (GPU) and/or an image signal processor. The processor 210 may include at least some (for example, a cellular module 221) of the components illustrated in FIG. 2. The processor 210 may load, into a volatile memory, commands or data received from at least one (e.g., a non-volatile memory) of the other components and may process the loaded commands or data, and may store various data in a non-volatile memory.

The communication module 220 may have a configuration equal or similar to that of the communication interface 170 of FIG. 1. The communication module 220 may include, for example, a cellular module 221, a Wi-Fi module 223, a BT module 225, a GNSS module 227 (e.g., a GPS module 227, a Glonass module, a Beidou module, or a Galileo module), an NFC module 228, and a Radio Frequency (RF) module 229. The cellular module 221, for example, may provide a voice call, a video call, a text message service, or an Internet service through a communication network. According to an embodiment of the present disclosure, the cellular module 221 may distinguish and authenticate the electronic device 201 in a communication network using a subscriber identification module (e.g.: SIM card) 224 (for example, the SIM card). According to an embodiment of the present disclosure, the cellular module 221 may perform at least some of the functions that the AP 210 may provide. According to an embodiment of the present disclosure, the cellular module 221 may include a communication processor (CP).

For example, each of the Wi-Fi module 223, the BT module 225, the GNSS module 227, and the NFC module 228 may include a processor for processing data transmitted/received through a corresponding module. According to an embodiment of the present disclosure, at least some (e.g., two or more) of the cellular module 221, the Wi-Fi module 223, the BT module 225, the GNSS module 227, and the NFC module 228 may be included in one Integrated Chip (IC) or IC package. The RF module 229, for example, may transmit/receive a communication signal (e.g., an RF signal). The RF module 229 may include, for example, a transceiver, a Power Amplifier Module (PAM), a frequency filter, a Low Noise Amplifier (LNA), and an antenna. According to another embodiment of the present disclosure, at least one of the cellular module 221, the WIFI module 223, the BT module 225, the GNSS module 227, and the NFC module 228 may transmit/receive an RF signal through a separate RF module. The subscriber identification module 224 may include, for example, a card including a subscriber identity module and/or an embedded SIM, and may contain unique identification information (e.g., an Integrated Circuit Card Identifier (ICCID)) or subscriber information (e.g., an International Mobile Subscriber Identity (IMSI)).

The memory 230 (e.g., the memory 130) may include, for example, an embedded memory 232 or an external memory 234. The embedded memory 232 may include at least one of a volatile memory (e.g., a Dynamic Random Access Memory (DRAM), a Static RAM (SRAM), a Synchronous Dynamic RAM (SDRAM), and the like) and a non-volatile memory (e.g., a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a flash memory (e.g., a NAND flash memory or a NOR flash memory), a hard disc drive, a Solid State Drive (SSD), and the like). The external memory 234 may further include a flash drive, for example, a Compact Flash (CF), a Secure Digital (SD), a Micro Secure Digital (Micro-SD), a Mini Secure Digital (Mini-SD), an eXtreme Digital (xD), a MultiMediaCard (MMC), a memory stick, or the like. The external memory 234 may be functionally and/or physically connected to the electronic device 201 through various interfaces.

The sensor module 240, for example, may measure a physical quantity or detect an operation state of the electronic device 201, and may convert the measured or detected information into an electrical signal. The sensor module 240 may include, for example, at least one of a gesture sensor 240A, a gyro sensor 240B, an atmospheric pressure sensor (barometer) 240C, a magnetic sensor 240D, an acceleration sensor 240E, a grip sensor 240F, a proximity sensor 240G, a color sensor 240H (e.g., red, green, and blue (RGB) sensor), a biometric sensor (medical sensor) 240I, a temperature/humidity sensor 240J, an illuminance sensor 240K, and a Ultra Violet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an Infrared (IR) sensor, an iris scan sensor, and/or a finger scan sensor. The sensor module 240 may further include a control circuit for controlling one or more sensors included therein. According to an embodiment of the present disclosure, the electronic device 201 may further include a processor configured to control the sensor module 240, as a part of the processor 210 or separately from the processor 210, and may control the sensor module 240 while the processor 210 is in a sleep state.

The input device 250 may include, for example, a touch panel 252, a (digital) pen sensor 254, a key 256, or an ultrasonic input device 258. The touch panel 252 may use, for example, at least one of a capacitive type, a resistive type, an infrared type, and an ultrasonic type. The touch panel 252 may further include a control circuit. The touch panel 252 may further include a tactile layer, and provide a tactile reaction to the user. The (digital) pen sensor 254 may include, for example, a recognition sheet which is a part of the touch panel or is separated from the touch panel. The key 256 may include, for example, a physical button, an optical key or a keypad. The ultrasonic input device 258 may detect, through a microphone (e.g., the microphone 288), ultrasonic waves generated by an input tool, and identify data corresponding to the detected ultrasonic waves.

The display 260 (e.g., the display 160) may include a panel 262, a hologram device 264, or a projector 266. The panel 262 may include a configuration identical or similar to the display 160 illustrated in FIG. 1. The panel 262 may be implemented to be, for example, flexible, transparent, or wearable. The panel 262 may be embodied as a single module with the touch panel 252. The hologram device 264 may show a three dimensional (3D) image in the air by using an interference of light. The projector 266 may project light onto a screen to display an image. The screen may be located, for example, in the interior of or on the exterior of the electronic device 201. According to an embodiment of the present disclosure, the display 260 may further include a control circuit for controlling the panel 262, the hologram device 264, or the projector 266.

The interface 270 may include, for example, a High-Definition Multimedia Interface (HDMI) 272, a Universal Serial Bus (USB) 274, an optical interface 276, or a D-subminiature (D-sub) 278. The interface 270 may be included in, for example, the communication interface 170 illustrated in FIG. 1. Additionally or alternatively, the interface 270 may include, for example, a Mobile High-definition Link (MHL) interface, a Secure Digital (SD) card/Multi-Media Card (MMC) interface, or an Infrared Data Association (IrDA) standard interface.

The audio module 280, for example, may bilaterally convert a sound and an electrical signal. At least some components of the audio module 280 may be included in, for example, the input/output interface 150 illustrated in FIG. 1. The audio module 280 may process voice information input or output through, for example, a speaker 282, a receiver 284, earphones 286, or the microphone 288. The camera module 291 is, for example, a device which may photograph a still image and a video. According to an embodiment of the present disclosure, the camera module 291 may include one or more image sensors (e.g., a front sensor or a back sensor), a lens, an Image Signal Processor (ISP) or a flash (e.g., LED or xenon lamp).

The power management module 295 may manage, for example, power of the electronic device 201. According to an embodiment of the present disclosure, the power management module 295 may include a Power Management Integrated Circuit (PMIC), a charger Integrated Circuit (IC), or a battery or fuel gauge. The PMIC may use a wired and/or wireless charging method. Examples of the wireless charging method may include, for example, a magnetic resonance method, a magnetic induction method, an electromagnetic wave method, and the like. Additional circuits (e.g., a coil loop, a resonance circuit, a rectifier, etc.) for wireless charging may be further included. The battery gauge may measure, for example, a residual quantity of the battery 296, and a voltage, a current, or a temperature while charging. The battery 296 may include, for example, a rechargeable battery and/or a solar battery.

The indicator 297 may display a particular state (e.g., a booting state, a message state, a charging state, or the like) of the electronic device 201 or a part (e.g., the processor 210) of the electronic device 201. The motor 298 may convert an electrical signal into a mechanical vibration, and may generate a vibration, a haptic effect, or the like. Although not illustrated, the electronic device 201 may include a processing device (e.g., a GPU) for supporting a mobile TV. The processing device for supporting a mobile TV may process, for example, media data according to a certain standard such as Digital Multimedia Broadcasting (DMB), Digital Video Broadcasting (DVB), or mediaFLO™.

Each of the above-described component elements of hardware according to the present disclosure may be configured with one or more components, and the names of the corresponding component elements may vary based on the type of electronic device. In various embodiments, the electronic device may include at least one of the above-described elements. Some of the above-described elements may be omitted from the electronic device, or the electronic device may further include additional elements. Also, some of the hardware components according to various embodiments may be combined into one entity, which may perform functions identical to those of the relevant components before the combination.

Figure 3:
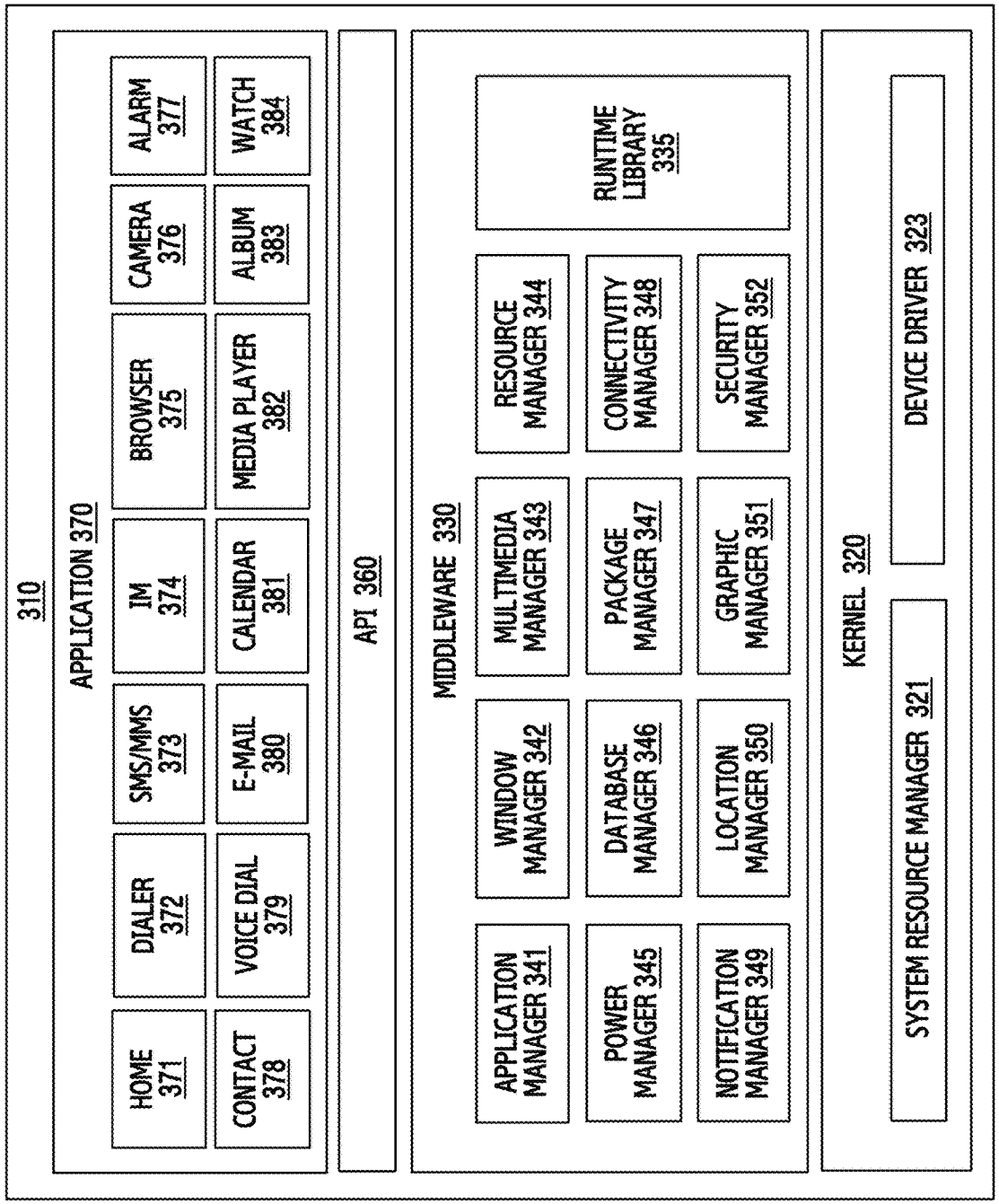
FIG. 3 is a block diagram illustrating a program module according to one exemplary embodiment.

FIG. 3 is a block diagram of a program module according to one embodiment of the present disclosure.

According to an embodiment of the present disclosure, the program module 310 (e.g., the program 140) may include an Operating System (OS) for controlling resources related to the electronic device (e.g., the electronic device 101) and/or various applications (e.g., the application programs 147) executed in the operating system. The operating system may be, for example, Android™, iOS™, Windows™, Symbian™, Tizen™, Bada™, or the like. The program module 310 may include a kernel 320, middleware 330, an API 360, and/or applications 370. At least some of the program module 310 may be preloaded on an electronic device, or may be downloaded from an external electronic device (e.g., the electronic device 102 or 104, or the server 106).

The kernel 320 (e.g., the kernel 141) may include, for example, a system resource manager 321 and/or a device driver 323. The system resource manager 321 may control, allocate, or collect system resources. According to an embodiment of the present disclosure, the system resource manager 321 may include a process management unit, a memory management unit, a file system management unit, and the like. The device driver 323 may include, for example, a display driver, a camera driver, a Bluetooth driver, a shared memory driver, a USB driver, a keypad driver, a Wi-Fi driver, an audio driver, or an Inter-Process Communication (IPC) driver.

For example, the middleware 330 may provide a function required in common by the applications 370, or may provide various functions to the applications 370 through the API 360 so as to enable the applications 370 to efficiently use the limited system resources in the electronic device. According to an embodiment of the present disclosure, the middleware 330 (e.g., the middleware 143) may include at least one of a run time library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module that a compiler uses in order to add a new function through a programming language while an application 370 is being executed. The runtime library 335 may perform input/output management, memory management, the functionality for an arithmetic function, or the like.

The application manager 341 may manage, for example, a life cycle of at least one of the applications 370. The window manager 342 may manage Graphical User Interface (GUI) resources used by a screen. The multimedia manager 343 may recognize a format required for reproduction of various media files, and may perform encoding or decoding of a media file by using a codec suitable for the corresponding format. The resource manager 344 may manage resources of a source code, a memory, and a storage space of at least one of the applications 370.

The power manager 345 may operate together with, for example, a Basic Input/Output System (BIOS) or the like to manage a battery or power source and may provide power information or the like required for the operations of the electronic device. The database manager 346 may generate, search for, and/or change a database to be used by at least one of the applications 370. The package manager 347 may manage installation or an update of an application distributed in a form of a package file.

For example, the connectivity manager 348 may manage wireless connectivity such as Wi-Fi or Bluetooth. The notification manager 349 may display or notify of an event such as an arrival message, promise, proximity notification, and the like in such a way that does not disturb a user. The location manager 350 may manage location information of an electronic device. The graphic manager 351 may manage a graphic effect which will be provided to a user, or a user interface related to the graphic effect. The security manager 352 may provide all security functions required for system security, user authentication, or the like. According to an embodiment of the present disclosure, when the electronic device (e.g., the electronic device 101) has a telephone call function, the middleware 330 may further include a telephony manager for managing a voice call function or a video call function of the electronic device.

The middleware 330 may include a middleware module that forms a combination of various functions of the above-described components. The middleware 330 may provide a module specialized for each type of OS in order to provide a differentiated function. Further, the middleware 330 may dynamically remove some of the existing components or add new components.

The API 360 (e.g., the API 145) is, for example, a set of API programming functions, and may be provided with a different configuration according to an OS. For example, in the case of Android or iOS, one API set may be provided for each platform. In the case of Tizen, two or more API sets may be provided for each platform.

The applications 370 (e.g., the application programs 147) may include, for example, one or more applications which may provide functions such as a home 371, a dialer 372, an SMS/MMS 373, an Instant Message (IM) 374, a browser 375, a camera 376, an alarm 377, contacts 378, a voice dial 379, an email 380, a calendar 381, a media player 382, an album 383, a clock 384, health care (e.g., measuring exercise quantity or blood sugar), or environment information (e.g., providing atmospheric pressure, humidity, or temperature information).

According to an embodiment of the present disclosure, the applications 370 may include an application (hereinafter, referred to as an "information exchange application" for convenience of description) that supports exchanging information between the electronic device (e.g., the electronic device 101) and an external electronic device (e.g., the electronic device 102 or 104). The information exchange application may include, for example, a notification relay application for transferring specific information to an external electronic device or a device management application for managing an external electronic device.

For example, the notification relay application may include a function of transferring, to the external electronic device (e.g., the electronic device 102 or 104), notification information generated from other applications of the electronic device 101 (e.g., an SMS/MMS application, an e-mail application, a health management application, or an environmental information application). Further, the notification relay application may receive notification information from, for example, an external electronic device and provide the received notification information to a user.

The device management application may manage (e.g., install, delete, or update), for example, at least one function of an external electronic device (e.g., the electronic device 102 or 104) communicating with the electronic device (e.g., a function of turning on/off the external electronic device itself (or some components) or a function of adjusting the brightness (or a resolution) of the display), applications operating in the external electronic device, and services provided by the external electronic device (e.g., a call service or a message service).

According to an embodiment of the present disclosure, the applications 370 may include applications (e.g., a health care application of a mobile medical appliance or the like) designated according to an external electronic device (e.g., attributes of the electronic device 102 or 104). According to an embodiment of the present disclosure, the applications 370 may include an application received from an external electronic device (e.g., the server 106, or the electronic device 102 or 104). According to an embodiment of the present disclosure, the applications 370 may include a preloaded application or a third party application that may be downloaded from a server. The names of the components of the program module 310 of the illustrated embodiment of the present disclosure may change according to the type of operating system.

According to various embodiments, at least a part of the programming module 310 may be implemented in software, firmware, hardware, or a combination of two or more thereof. At least some of the program module 310 may be implemented (e.g., executed) by, for example, the processor (e.g., the processor 210). At least some of the program module 310 may include, for example, a module, a program, a routine, a set of instructions, and/or a process for performing one or more functions.

The term "module" as used herein may, for example, mean a unit including one of hardware, software, and firmware or a combination of two or more of them. The "module" may be interchangeably used with, for example, the term "unit," "logic," "logical block," "component," or "circuit." The "module" may be mechanically or electronically implemented. For example, the "module" according to the present disclosure may include at least one of an Application-Specific Integrated Circuit (ASIC) chip, a Field-Programmable Gate Arrays (FPGA), and a programmable-logic device for performing operations which has been known or are to be developed hereinafter. According to various embodiments, at least some of the devices (for example, modules or functions thereof) or the method (for example, operations) according to the present disclosure may be implemented by a command stored in a computer-readable storage medium in a programming module form. The instruction, when executed by a processor (e.g., the processor 120), may cause the one or more processors to execute the function corresponding to the instruction. The computer-readable recoding media may be, for example, the memory 130.

Figure 4:
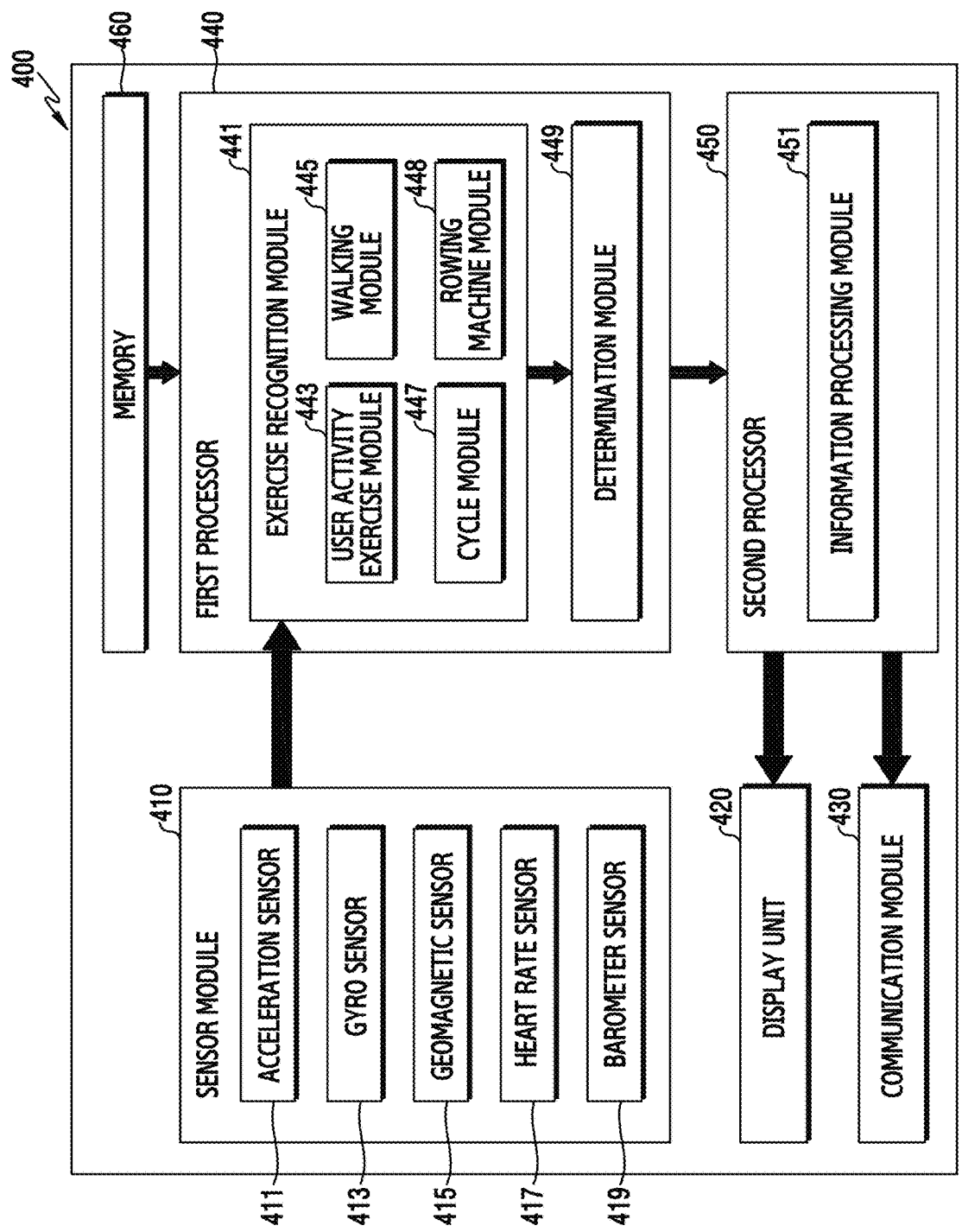
FIG. 4 is a block diagram illustrating structures of an electronic device according to one exemplary embodiment.

FIG. 4 is a block diagram illustrating structures of an electronic device according to one exemplary embodiment.

Referring to FIG. 4, an electronic device 400 (e.g., the electronic device 101) may include a sensor module 410, a display unit 420, a communication module 430, a first processor 440, a second processor 450, and a memory 460. The memory 460 may be included in the first processor 440 or located outside the first processor 440, and may be operatively coupled with the first processor 440.

The sensor module 410 may continuously or periodically sense information, depending on the user's movement. The sensor module 410 may include at least one of an acceleration sensor 411, a gyro sensor 413, a geomagnetic sensor 415, a heart rate sensor 417, and a barometer sensor 419. The acceleration sensor 411 is a sensor for measuring an acceleration acting on x, y, and z axes, and may use the measured acceleration to estimate force applied to the electronic device 400. The gyro sensor 413 is a sensor for measuring a posture change of the electronic device 400, and may measure a position and directivity using the mechanical motion of a rotating object in the gyro sensor 413. The geomagnetic sensor 415 is a sensor used to detect geomagnetism, and may measure the magnitude and direction of the geomagnetism.

The heart rate sensor 417 may continuously or periodically sense biometric information, such as heart rate, of the user wearing the electronic device 400. The barometer sensor 419 may be a sensor for sensing an altitude change of the electronic device 400. For example, the barometer sensor 419 may measure whether the user is moving while gaining or losing altitude. The sensor module 410 may be the sensor module 240 of FIG. 2. Therefore, the sensor module 410 may further include other sensors not shown in FIG. 4. The sensor module 410 may deliver measured or sensed sensor data to the first processor 440.

The first processor 440 may be always operating (e.g., in an activated state or an operational mode) when power is supplied to the electronic device 400. For example, the first processor 440 may be always awake to receive sensor data from the sensor module 410 while power is supplied to the electronic device 400. The first processor 440 may always be in the awake state regardless of whether the display unit 420 of the electronic device 400 is turned on or off. The first processor 440 may be driven with lower power than the second processor 450. The first processor 440 may determine the user's activity state based on sensor data received from the sensor module 410. For example, the first processor 440 may determine whether the user's activity is daily-life movement, general exercise, or specific exercise. The first processor 440 may deliver the determined user's activity information to the second processor 450.

The first processor 440 according to one exemplary embodiment may monitor the user's activity state on the basis of the sensor data received from the acceleration sensor 411. If a difference between two data points in the sensor data is less than a threshold, the first processor 440 may determine the user's activity information as "daily-life movement". For example, the daily-life movement may be a movement such as moving the arm while sitting. Such daily-life movements occur frequently outside of specific exercise periods, such as when the user is walking, running, strength exercise, sports, etc. If the difference between two data points in the senor data is greater than or equal to the threshold, the first processor 440 may determine whether the sensor data includes regular periods. If the period of the sensor data is regular or repetitive, the first processor 440 may determine the user's activity information as "general exercise." For example, the general exercise may include the regular exercises such as walking, running, or the like and the repetitive exercise such as using elliptical or rowing machine, or the like. According to one exemplary embodiment, in order to determine the type of exercise more precisely, the first processor 440 may determine the exercise type based on the sensor data from at least one of the gyro sensor 413, the geomagnetic sensor 415, and the heart rate sensor 417.

If the difference between two data points in the sensor data of the acceleration sensor 411 is greater than or equal to the threshold and the period of the sensor data is irregular, the first processor 440 may determine whether the user's movement continues for a given amount of time. If the user's movement is continuous, the first processor 440 may determine the user's activity information as "user activity exercise." The user activity exercise may imply irregular exercise such as basketball, baseball, soccer, or the like. For example, in case of the soccer, the user's movement is irregular because during the period of exercise, i.e. during the soccer match, the user's movement may include breaks, such as when the user is standing or when the user is walking slowly. In this case, conventionally, when a break occurs, an electronic device may determine that the user is no longer exercising, even though the user is still participating in the soccer match. In the disclosed exemplary embodiments, algorithms for determining an irregular user activity as an exercise may be used.

The first processor 440 according to one exemplary embodiment may include an exercise recognition module 441 and a determination module 449. The exercise recognition module 441 may use sensor data received from the sensor module 410 to recognize the user's activity state. The exercise recognition module 441 may include a module capable of recognizing a regular exercise such as walking, running, or the like, a repetitive exercise such as cycling, using a rowing machine, or the like, and a user activity exercise such as basketball, soccer, or the like. For example, the exercise recognition module 441 may include a user activity exercise module 443, a walking module 445, a cycle module 447, and a rowing machine module 448. Each of the modules included in the exercise recognition module 441 may determine its corresponding exercise based on the user's movement. The exercise recognition module 441 may deliver the recognized (or determined) user's activity information to the determination module 449.

For example, if the period of the sensor data is irregular and is continued with at least a specific intensity, the user activity exercise module 443 may recognize this as "user activity exercise." If the sensor data includes a periodic or regular pattern, the walking module 445 may recognize this as "walking." If the sensor data represents a repetitive pattern and the sensor data is showing a vertical acceleration, an elliptical module (not shown in FIG. 4) may recognize this as "elliptical." If the sensor data represents the repetitive pattern and the sensor data is showing a horizontal acceleration, the rowing machine module 448 may recognize this as "rowing machine."

The determination module 449 may finally determine the user's activity information recognized or determined by the exercise recognition module 441. For example, the determination module 449 may use at least one of a size, repeatability, regularity, and continuity of the sensor data to determine whether the user's activity information is a daily-life movement, a general exercise, or a user activity exercise.

The second processor 450 may optionally operate in a selective manner. For example, if the display unit 420, which may include an input unit such as a touch input sensor, is turned on, acquires information, or scans information, then the second processor 450 may be active (e.g., an operational mode). In addition, if the display unit 420 is turned off, the second processor 450 may be inactive (e.g., in a sleep mode). While inactive (e.g., in the sleep mode), the second processor 450 may periodically wake up when it is programmed to, for example, periodically operate an sensor to scan for data. The second processor 450 may acquire communication information from the communication module 430. The communication information may include base station information, wireless network information, or location information, etc. The display unit 420 may be the display 260 of FIG. 2. In addition, the communication module 430 may be, for example, the communication module 220 of FIG. 2.

The second processor 450 according to one exemplary embodiment may include an information processing module 451. The information processing module 451 may receive information (e.g., activity information) regarding the user's current state from the first processor 440. The second processor 450 may continuously receive the user's activity information from the first processor 440 when the second processor 450 is active, and may receive the user's activity information periodically or optionally from the first processor 440 when the second processor 450 is inactive (e.g. in the sleep mode). The information processing module 451 may provide the user with a user interface associated with the activity information received from the first processor 440. For example, the information processing module 451 may display information to the user via the display unit 420, or may output a sound associated with the information via an audio unit (e.g., the audio module 280). The information processing module 451 may also transmit the user's state information to another electronic device connected to the electronic device 400 by using the communication module 430.

According to one exemplary embodiment, an electronic device (e.g., the electronic device 101, the electronic device 400) may include one or more sensor modules (e.g., the sensor module 240, the sensor module 410), at least one memory (e.g., the memory 130, the memory 230, the memory 460), a display (the display 160, the display 260, the display 420), and a first processor (e.g., the first processor 440) or second processor (e.g., the processor 120, the processor 210, the second processor 450) operatively coupled to the one or more sensor modules, the at least one memory, and/or the display. The first processor may be configured to acquire sensor data from at least one sensor module among the one or more sensor modules, calculate a difference between at least two data points in the acquired sensor data, determine user's activity information based on at least one of a period of the sensor data, a magnitude of the difference, and a change amount of the difference, and deliver the activity information to the second processor. The second processor may be configured to display, on the display, a user interface related to the user's activity information delivered from the first processor.

The first processor may be configured to determine whether the period of the sensor data is regular if the difference is greater than or equal to a first threshold.

The first processor may be configured to determine the user's activity information as a user activity exercise if the difference is greater than or equal to a first threshold, if the period of the sensor data is irregular, and if the change amount of the difference is greater than a second threshold.

The first processor may be configured to determine the user's activity information as a general exercise if the difference is greater than or equal to a first threshold and if the period of the sensor data is regular.

The first processor may be configured to determine the user's activity information as a daily-life movement if the difference is less than or equal to a first threshold.

The first processor may be configured to determine, if the user's activity information is a user activity exercise, whether the user activity exercise is maintained based on an interval between a recent exercise time and a current time.

The first processor may be configured to determine an exercise intensity based on the change amount of the difference during a specific period of time. The second processor may be configured to provide information related to the exercise intensity.

If the period of the sensor data is regular and if the difference is greater than or equal to a first threshold, the first processor may be configured to acquire sensor data from another sensor module different from the at least one sensor module.

The first processor may be configured to determine an exercise type for the user's activity information based on the sensor data from the other sensor module.

The electronic device may be an electronic device wearable on a user's body.

The first processor may be always in an active state, and the second processor may be configured to selectively switch between the active state and an inactive state.

The at least one memory may be integrated with the first processor or may be located outside the first processor.

Figure 5:
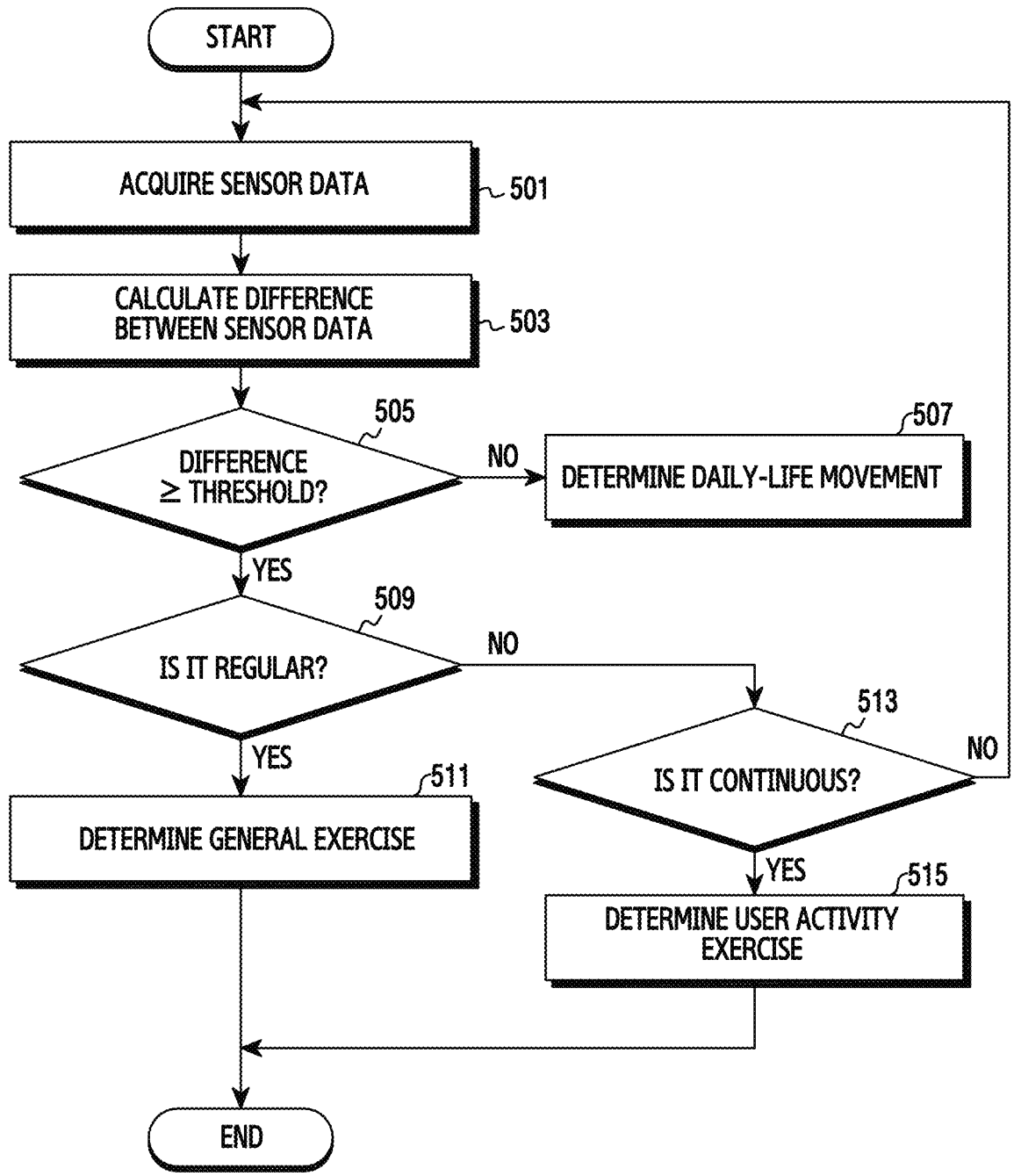
FIG. 5 is a flowchart illustrating a method of operating an electronic device according to one exemplary embodiment.

FIG. 5 is a flowchart illustrating a method of operating an electronic device according to one exemplary embodiment.

Referring to FIG. 5, in operation 501, the electronic device 400 (e.g., the first processor 440) may acquire sensor data. The first processor 440 may acquire at least one piece of sensor data associated with a user's movement from a sensor module (e.g., the sensor module 410). The first processor 440 may store the acquired sensor data in a memory (e.g., the memory 460), and may monitor the data, as explained below in connection with the rest of FIG. 5. For example, the first processor 440 may acquire the sensor data from an acceleration sensor (e.g., the acceleration sensor 411).

The electronic device 400 according to one exemplary embodiment may be a device that can be worn on the user's body, such as a wearable device, to detect the user's movement. Alternatively, the electronic device 400 may receive the sensor data from a wearable device communicatively coupled to the electronic device 400. The wearable device in turn may have the sensor module 410.

The first processor 440 may drive only one sensor (or a plurality of sensors) at a time instead of driving all sensors simultaneously. For example, each sensor may consume power at different rates. The reliability of determining the user's activity based on each sensor's data may also be different for each sensor. The first processor 440 may operate a sensor based on the power consumption of the sensor and/or the user's activity state. Alternatively, the electronic device 400 may have an always-on sensor because it has the lowest power consumption. The first processor 440 may monitor sensor data acquired from the always-on sensor (e.g., a first sensor) and, depending on the sensor data for the first sensor, determine whether to drive another sensor (e.g., a second sensor).

For example, the first processor 440 may primarily drive the acceleration sensor 411 to determine the user's activity state. "Primarily drive" may mean that the acceleration sensor 411 is always on and sensing acceleration data. If the user's activity state is a general exercise, the first processor 440 may additionally drive the gyro sensor 413, the geomagnetic sensor 415, or the heart rate sensor 417 to determine the exercise type.

In operation 503, the electronic device 400 (e.g., the first processor 440) may calculate a difference between two data points in the sensor data. For example, the first processor 440 may cancel noise from the acquired sensor data, and may calculate a difference between two pieces of sensor data after the noise cancellation. Noise cancellation may be used so that the monitored sensor data is more accurate. For example, the first processor 440 may cancel noise from the sensor data by using a low pass filter, an average filter, or the like. The two data points may be separated in time by a predetermined time interval, and the difference may include a plurality of values generated continuously as the user exercises. For example, a first difference may be calculated between the sensor data at time index 0 minute and 2 minute. A second difference may be calculated between the sensor data at time index 1 minute and 3 minute, a third difference may be calculated between the sensor data at time index 2 minute and 4 minute, and so forth. The first processor 440 may store the calculated difference in a memory (e.g., the memory 460).

In operation 505, the electronic device 400 (e.g., the first processor 440) may determine whether the calculated difference is greater than or equal to a threshold. The difference and the threshold may be associated with the intensity of the user's movement. The threshold may be preset by the first processor 440 or may be pre-stored in the memory 460. Alternatively, the threshold may be adjusted according to the user's activity intensity, and may be designated differently depending on the user's weight, gender, or the like. The first processor 440 may set the threshold differently based on the calculated differences. This may be done so that daily-life movements of the use are not mistaken for exercise. For example, the threshold may be small when the user has just started exercising, and the threshold may become greater as the exercise continues. Therefore, the magnitudes of the threshold and the previously calculated difference may be correlated. That is, if the previous difference is relatively large, the threshold may be adjusted to be relatively large, and if the previous difference is relatively small, the threshold may be adjusted to be relatively small.

Accordingly, the first processor 440 according to one exemplary embodiment may preset a relatively small initial threshold because prior to exercise, when the user is only performing daily-life movements, the previously calculated difference in the sensor data is also relatively small. For example, the first processor 440 may set the initial threshold to correspond to a movement intensity greater than intensities of general daily-life movements.

The first processor 440 may perform operation 509 if the difference is greater than or equal to the threshold value, and may perform operation 507 if the difference is less than the threshold.

If the difference is less than the threshold, in operation 507, the electronic device 400 (e.g., the first processor 440) may determine that the user's movement is a daily-life movement. As explained above, the daily-life movements are ordinary, non-exercise movements performed in daily life, and may not be regarded as exercise. For example, if the movement is detected but the detected movement only continues for a relatively short period of time (e.g., 1 second, 1 minute, 5 minutes, 10 minutes, etc.), the first processor 440 may determine the movement to be daily-life movement. For example, daily-life movements may include moving an arm when the user is seated (e.g., keyboard typing), walking over a short distance (e.g., going to the restroom), running over a short distance (e.g., running to catch the bus), or the like.

If the difference is greater than or equal to the threshold, in operation 509, the electronic device 400 (e.g., the first processor 440) may determine whether the user's movement is regular. According to one exemplary embodiment, a difference value and sensor data for a specific period of time (e.g., 10 minutes) may be needed to determine whether the user's movement is regular. As described above, in case of daily-life movements, the movement intensity is not great (e.g., a difference value is less than a threshold), does not have persistency (e.g., less than 10 seconds), and is irregular, whereas when the user is exercising (e.g., walking, cycle, etc.), the sensor data may have a regularity. The first processor 440 may determine whether the difference value for the specific period of time is greater than or equal to the threshold and whether a period of the sensor data is regular.

The first processor 440 may perform operation 511 if it is regular, and may perform operation 513 if it is irregular.

If it is regular, in operation 511, the electronic device 400 (e.g., the first processor 440) may determine the user's movement to be general exercise. General exercise may include regular or repetitive exercises such as walking, running, cycle, using the elliptical and rowing machines, or the like. If general exercise is determined, the first processor 440 may further drive other sensors (e.g., the gyro sensor 413, the geomagnetic sensor 415, and the heart rate sensor 417) to determine the type of general exercise.

Further, the first processor 440 may determine the type of exercise and monitor whether the exercise is terminated. The first processor 440 may store general exercise information (e.g. the sensor data) in a memory (e.g., the memory 460) until the general exercise is terminated. If the type of exercise is determined or if the exercise is terminated, the first processor 440 may deliver the general exercise information to the second processor 450. The second processor 450 may provide a user interface for the general exercise information at the request of the user. The user interface may consist of at least one of text, image, and video. For example, the user interface may include at least one of an exercise time, an exercise distance, an exercise type, an exercise intensity, and consumed calories.

If it is irregular, in operation 513, the electronic device 400 (e.g., the first processor 440) may determine whether the user's movement is continuous. For example, in case of daily-life movements, the movement intensity may not be great, may not have persistency, and may be irregular. However, when the user participates in sports such as baseball, soccer, badminton, the user's movement intensity may be great occasionally but have a relatively short duration (e.g., when the user is sprinting). The user's movements may also be irregular as the user takes breaks during the game (e.g., standing during a soccer match when the user is not near the ball or standing on base during a baseball game). Therefore, if changes in the difference for a specific period of time is greater than or equal to a threshold, it may be determined that the user's movement is continuous. Thus, despite irregular sensor data during the specific period of time, the first processor 440 may determine this as a user activity exercise.

If the user movement is continuous, the first processor 440 may perform operation 515, and otherwise, may return to operation 501.

If it is continuous, in operation 515, the electronic device 400 (e.g., the first processor 440) may determine the user's movement as a user activity exercise. The user activity exercise may imply irregular exercise such as exercise taking place during sports. For example, the discontinuous exercise may be an exercise in which a movement is detected irregularly such that the movement may or may not be detected despite of a relative constant motion or posture. In addition, the irregular exercise may imply an exercise of which a motion, a posture, or a movement is detected irregularly such as basketball, baseball, soccer, badminton, or the like. In this case, the first processor 440 may not be able to identify the specific sport the user is undertaking.

Further, the first processor 440 according to one exemplary embodiment may monitor whether the user activity exercise is terminated. The first processor 440 may store the user activity exercise information (e.g. the sensor data) in a memory (e.g., the memory 460) until the user activity exercise is terminated. If it is determined as the user activity exercise or if the user activity exercise is terminated, the first processor 440 may deliver the user activity exercise information to the second processor 450. The second processor 450 may provide a user interface for the user activity exercise information at the request of the user. The user interface may consist of at least one of text, image, and video. For example, the user interface may include at least one of an exercise time, an exercise distance, an exercise type, an exercise intensity, and consumed calories.

The first processor 440 may return to operation 501 if it is determined that the user's movement is irregular and not persistent. For example, after monitoring the sensor data for a specific period of time (e.g., 10 minutes), the user's movement may be sufficiently irregular that the first processor 440 cannot determine whether the user movement is daily-life movement, general exercise or user activity exercise. In this case, for more accurate determination, the first processor 440 may return to operation 501 and use a longer monitoring period (e.g., 15 minutes, 20 minutes). The first processor 440 may perform operation 501 to operation 513 again on the basis of the longer monitoring period.

Figure 6:
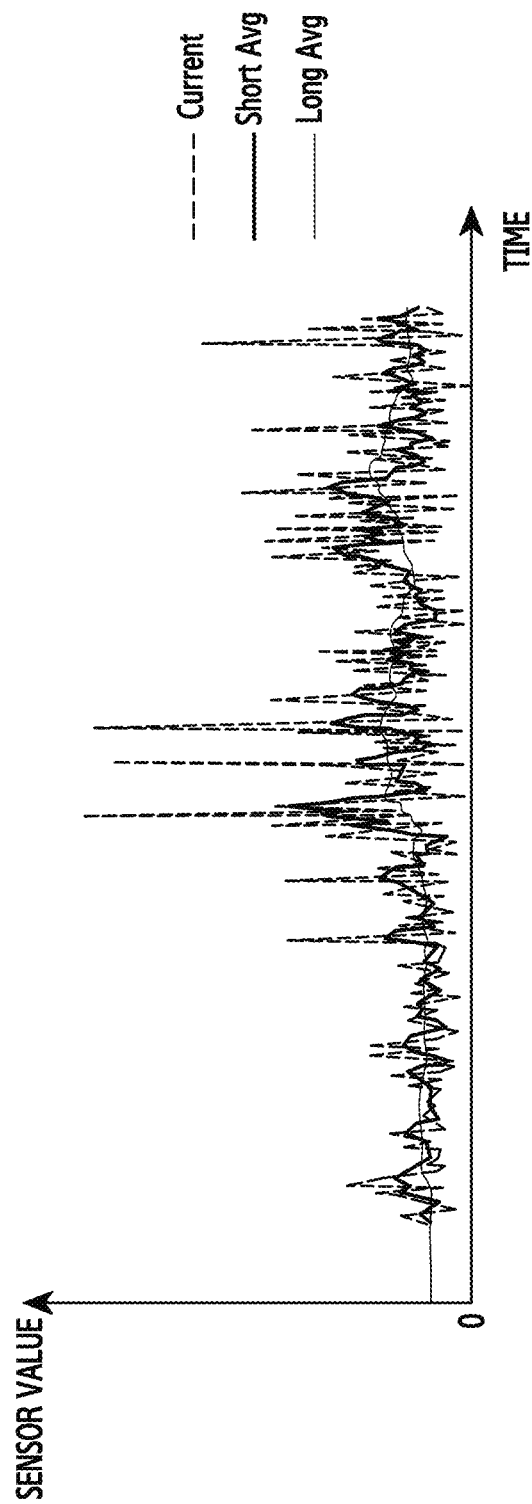
FIG. 6 is a graph for illustrating an example of recording a user's movement based on sensor data according to one exemplary embodiment.

FIG. 6 is a graph for illustrating an example of recording a user's movement based on sensor data according to one exemplary embodiment.

Referring to FIG. 6, the current sensor values (e.g., the dotted line, Current) are the current normalized acceleration sensor data based on the user's movement obtained by the acceleration sensor. The short average values (e.g., the bold solid line, Short Avg) are values obtained when a specific number (e.g., 10) of samples of current sensor values are noise-filtered and averaged. The long average values (e.g., the thin solid line, Long Avg) are values obtained when a specific number (e.g., 100) of samples of current sensor values are noise-filtered and averaged. The long average value may have less noise interference than the short average value but may have less variation in magnitude that corresponds to exercise intensity. The electronic device 400 (e.g., the first processor 440) may determine a threshold based on the short average value or the long average value. Upon detecting differences between data points in the sensor data are greater than or equal to the determined threshold, the first processor 440 may determine the user's movement as a general exercise or a user activity exercise.

Figure 7:
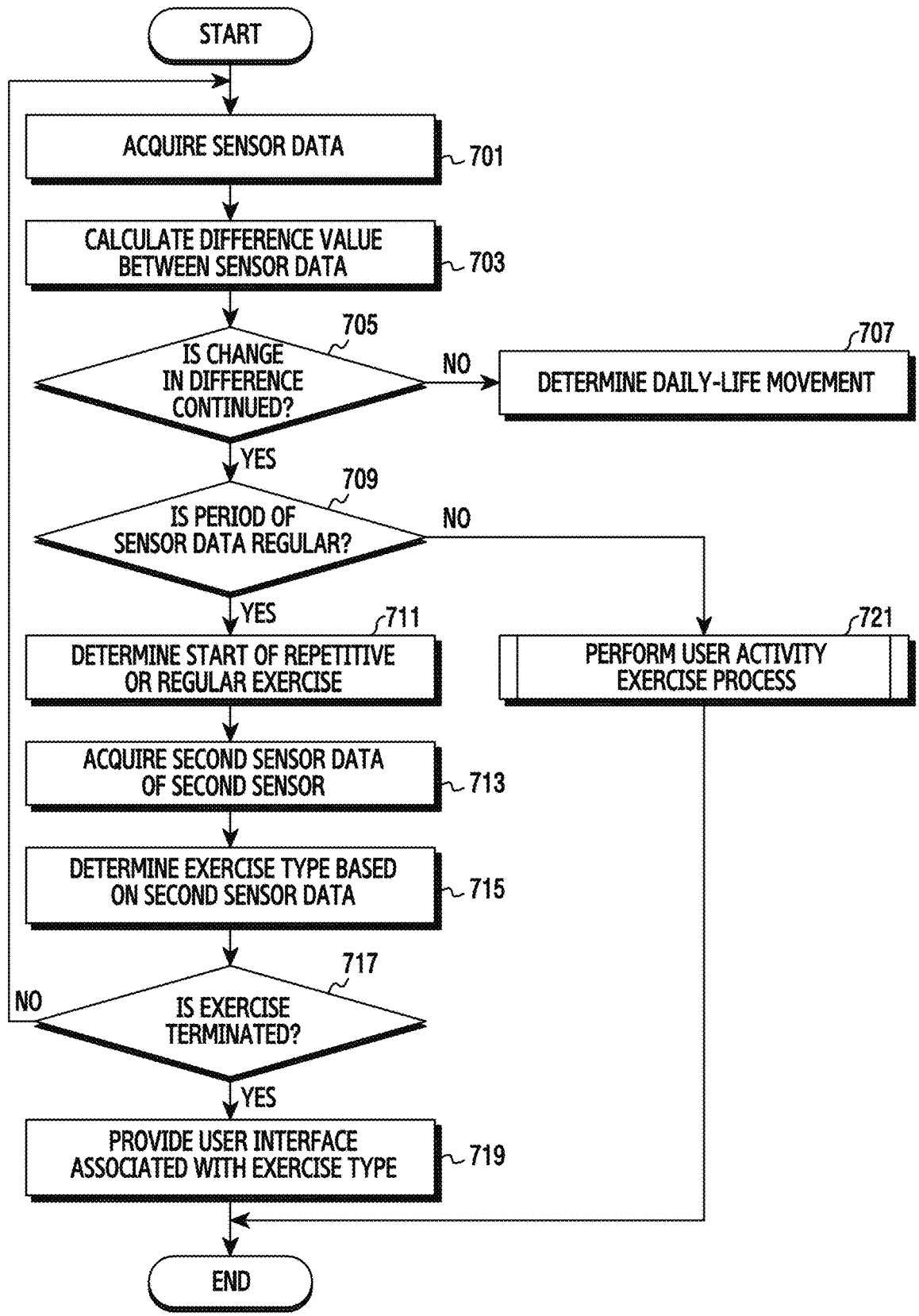
FIG. 7 is a flowchart illustrating a method of recognizing a user activity of an electronic device according to one exemplary embodiment.

FIG. 7 is a flowchart illustrating a method of recognizing a user activity of an electronic device according to one exemplary embodiment.

Referring to FIG. 7, in operation 701, the electronic device 400 (e.g., the first processor 440) may acquire sensor data. The first processor 440 may acquire at least one piece of sensor data related to a user's movement from a sensor module (e.g., the sensor module 410). Since operation 701 is identical or similar to operation 501 of FIG. 5 described above, detailed descriptions thereof may be omitted.

In operation 703, the electronic device 400 (e.g., the first processor 440) may calculate a difference between two data points in the sensor data. For example, the first processor 440 may cancel noise from the acquired sensor data, and may calculate a difference between two pieces of sensor data. Since operation 703 is identical or similar to operation 503 of FIG. 5 described above, detailed descriptions thereof may be omitted.

In operation 705, the electronic device 400 (e.g., the first processor 440) may determine whether a change in the difference is continued for a specific period of time. The first processor 440 may determine whether the user's movement is continued by determining whether there is a change in the difference between two pieces of successive sensor data obtained on a real time basis or periodically over the specific period of time. For example, the change in the difference may be found in the short average value (Short Avg) described in FIG. 6. If there is a change in the difference, the short average value may also change. Alternatively, if there is no change in the difference, the short average value may be unchanged.

The first processor 440 may perform operation 709 if the change in the difference is continued, and may perform operation 707 if the change in the difference is not continued.

If the change in the difference is not continued, in operation 707, the electronic device 400 (e.g., the first processor 440) may determine the user's movement to be a daily-life movement. The daily-life movements are ordinary, non-exercise movements performed in daily life, and may not be regarded as exercise. For example, if the movement is detected but the detected movement only continues for a relatively short period of time (e.g., 1 second, 1 minute, 5 minutes, 10 minutes, etc.), the first processor 440 may determine the movement to be daily-life movement.

If the change in the difference is continued, in operation 709, the electronic device 400 (e.g., the first processor 440) may determine whether the sensor data is regular. Referring to FIG. 6, the first processor 440 may determine whether the sensor data over a specific period of time (e.g., 5 minutes, 10 minutes, etc.) has a specific pattern. If so, the first processor 440 may determine that the sensor data over that period of time is regular.

The first processor 440 may perform operation 711 if it is regular, and may perform operation 721 if it is irregular.

If it is regular, in operation 711, the electronic device 400 (e.g., the first processor 440) may determine the user's movement as the start of repetitive or regular exercise. For example, the repetitive or regular exercise may be a general exercise such as walking, running, cycle, using elliptical and rowing machines, etc. The first processor 440 may determine the start time to be when the sensor data is determined as being regular.

In operation 713, the electronic device 400 (e.g., the first processor 440) may acquire second sensor data of a second sensor. The second sensor may be a different sensor than the one used in operation 701. The first processor 440 may choose the second sensor based on the sensor data acquired in operation 701. For example, if the sensor data acquired in operation 701 is regular and if it indicates that the user is at a speed greater than typical running speed, the first processor 440 may tentatively predict that the user is cycling. The first processor 440 may then drive a gyro sensor, as the second sensor, for detecting sensor data in the vertical direction.

Alternatively, if the sensor data acquired in operation 701 is regular and indicates the user at a specific speed, the first processor 440 may tentatively predict that the user is using a rowing machine. The first processor 440 may then drive a gyro sensor or geomagnetic sensor, as the second sensor, for detecting sensor data in the horizontal direction. In yet another example, if the acquired sensor data is regular pattern and indicates the user speed is less than a specific speed, the first processor 440 may tentatively determine that the user is walking. The first processor 440 may then drive the gyro sensor as the second sensor to acquire more accurate posture information. Alternatively, the first processor 440 may drive a heart rate sensor to measure the user's heart rate. On the other hand, if it is determined that the user is walking, the first processor 440 may not perform operations 713 to operation 715.

In operation 715, the electronic device 400 (e.g., the first processor 440) may determine the exercise type on the basis of the second sensor data. For example, the types of general exercise may include walking, jogging, running, swimming, cycle, climbing, repetitive exercises (e.g., using elliptical or rowing machines, rope jumping), or the like. Exercise categories may not be perfectly distinguishable due to the complexity of the sensor data, but the more regular the movement and the stronger the intensity, the easier it is to categorize the movement. In addition, the exercise type may be determined more accurately when a greater amount of sensor data is used. Therefore, the first processor 440 may determine the exercise type based on the second sensor data.

In operation 717, the electronic device 400 (e.g., the first processor 440) may determine whether the general exercise is terminated. The first processor 440 may store general exercise information (e.g. the sensor data) in a memory (e.g., the memory 460) until the general exercise is terminated. For example, in case of the general exercise, it may be determined that the exercise is terminated if the intensity of the user's movement, as indicated by the sensor data acquired in operation 701 and/or by the second sensor data, has fallen below the threshold or the user's movements are no longer regular. Alternatively, the first processor 440 may determine that the exercise is terminated if the second sensor data is not detected.

The first processor 440 may perform operation 719 if it is determined that the exercise is terminated, and may return to operation 701 if it is determined that the exercise is not terminated. Although it is shown in the figure that the procedure returns to operation 701, it is also possible to return to operation 713.

When the exercise is terminated, in operation 719, the electronic device 400 (e.g., the first processor 440) may deliver the general exercise information to the second processor 450. The electronic device 400 (e.g., the second processor 450) may provide a user interface for the exercise type at the request of the user. The user interface may consist of at least one of text, image, and video. For example, the user interface may include at least one of an exercise time, an exercise distance, an exercise type, an exercise intensity, and consumed calories. The first processor 440 or the second processor 450 may calculate consumed calories by using at least one of the exercise time, the exercise distance, the exercise type, and the exercise intensity.

If the period of the sensor data is irregular, in operation 721, the electronic device 400 (e.g., the first processor 440) may perform a user activity exercise process. For example, the user activity exercise process may include an action performed when the user's movement corresponds to a user activity exercise, such as participating in a sports event. The first processor 440 may determine the user's movement as the user activity exercise and store information regarding the user activity exercise in a memory (e.g., the memory 460). And if the user activity exercise is terminated, the first processor 440 may deliver the user activity exercise information to the second processor 450. The second processor 450 may provide a user interface for the user activity exercise information at the request of the user.

Figure 8A:
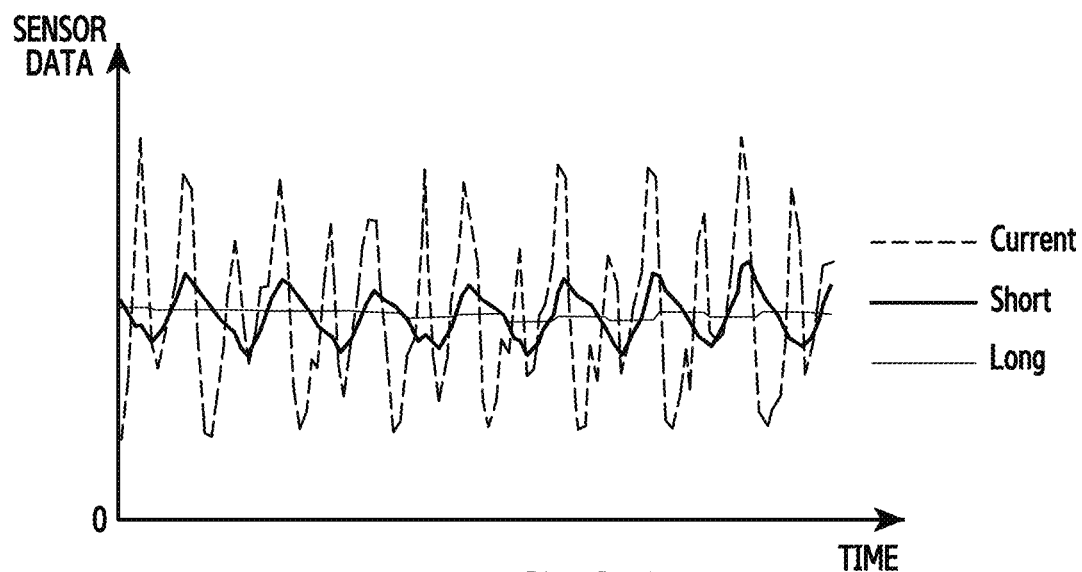
FIG. 8A and FIG. 8B are graphs illustrating sensor data for regular exercises according to one exemplary embodiment.
Figure 8B:
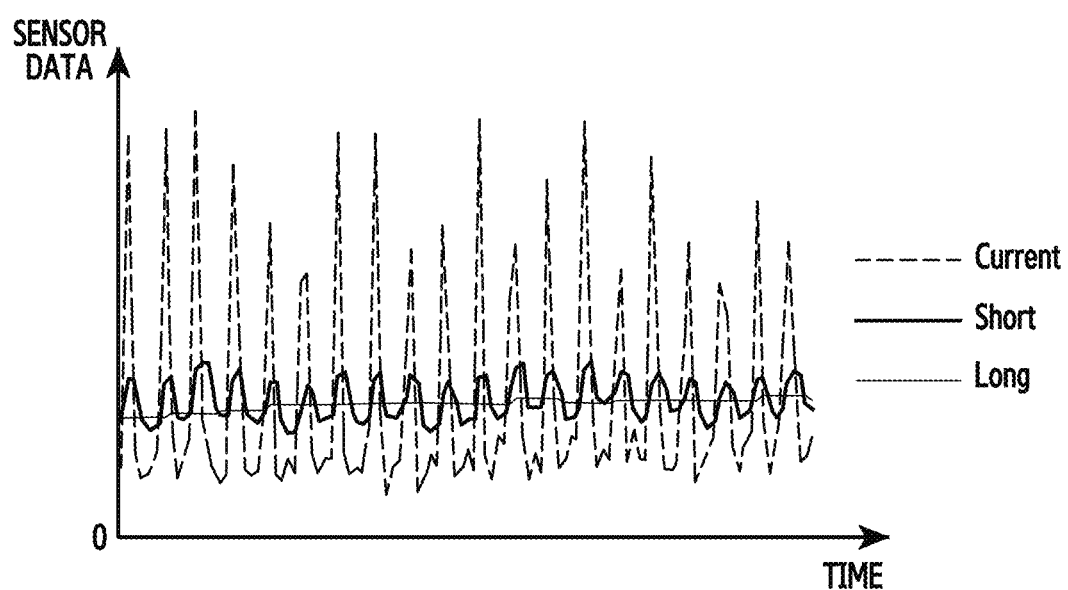

FIGS. 8A and 8B are graphs illustrating sensor data for regular exercises according to one exemplary embodiment.

FIG. 8A represents a sensor data graph for walking exercise, and FIG. 8B represents a sensor data graph for power walking. Sensor data shows regular patterns in both cases. For example, the short average values (e.g., the bold solid line, Short Avg) may indicate specific periods in proportion to the current sensor value (e.g. the dotted line, Current), whereas the long average values (e.g., the thin solid line, Long Avg) may indicate specific magnitudes of the current sensor value. Therefore, for example using the long average values, it can be seen that power walking has a higher intensity than ordinary walking. Using the short average values, it can be seen that power walking also has a shorter period than ordinary walking. The first processor 440 may determine whether the user's movement is ordinary walking or power walking by considering the current sensor values, the short average values and the long average values.

Figure 9A:
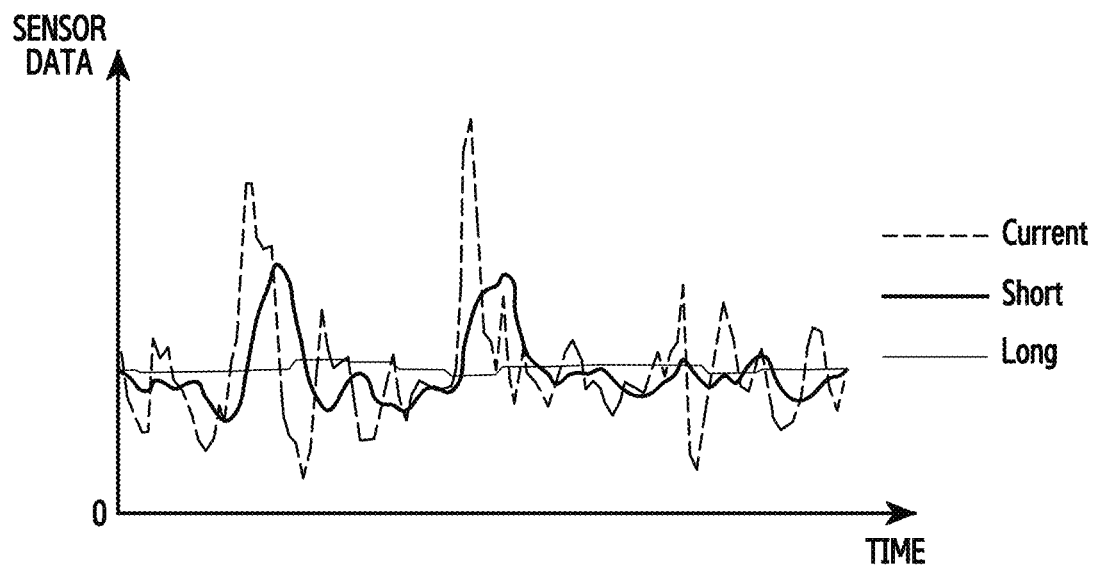
FIG. 9A and FIG. 9B are graphs illustrating sensor data for irregular exercises according to one exemplary embodiment.
Figure 9B:
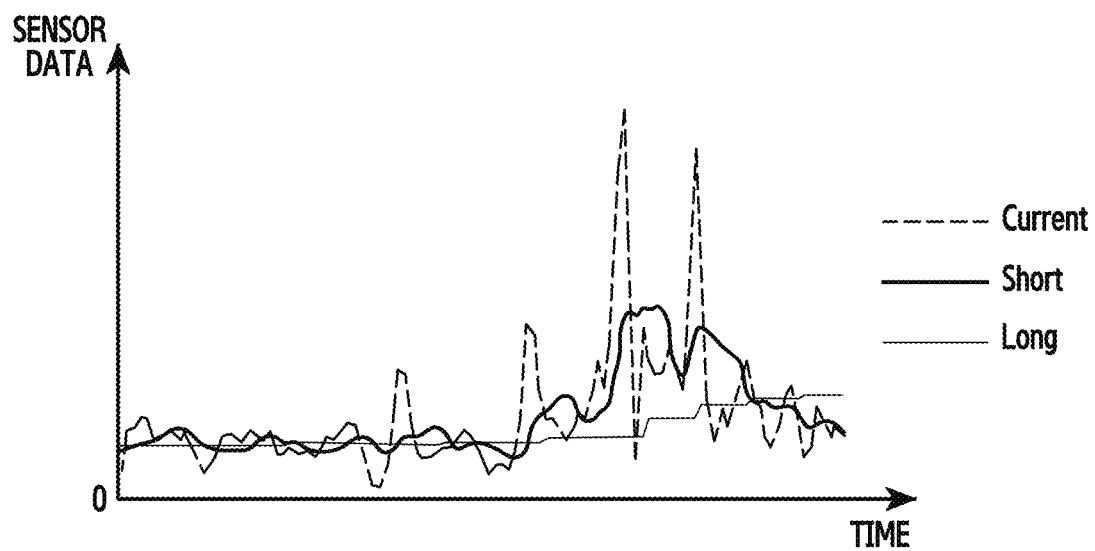

FIGS. 9A and 9B are graphs illustrating sensor data for irregular exercises according to one exemplary embodiment.

FIG. 9A represents a sensor data graph for a badminton exercise during a first time period, and FIG. 9B represents a sensor data graph for a badminton exercise during a second time period. In both FIGS. 9A and 9B, sensor data shows irregular patterns, so that the first processor 440 may use this data to distinguish from, for example, walking. For example, the short average values are increased or decreased in proportion to the current sensor value. Unlike the short average values shown in FIG. 8, the short average values in FIG. 9 indicates irregular periods. Further, unlike those in FIG. 8, the long average values in FIG. 9 shows changing magnitudes, indicating varying movement intensity. This can also be used to distinguish from ordinary walking or power walking.

For example, when participating in sports activity such as basketball, baseball, soccer, badminton, or the like, the detected long average values may exhibit greater variation due to frequent transitions in user movements from low-intensity to high-intensity actions and vice versa, such as going from a light jog to a sprint. That is, sports activities are characterized by strong movements which are not repetitive, and whether the first processor 440 may determine user movement to be sports activity when carefully analyzing those characteristics. Therefore, the first processor 440 may determine whether the user's movement is a user activity exercise on the basis of differences between data points in the sensor data and variations in the differences.

Figure 10:
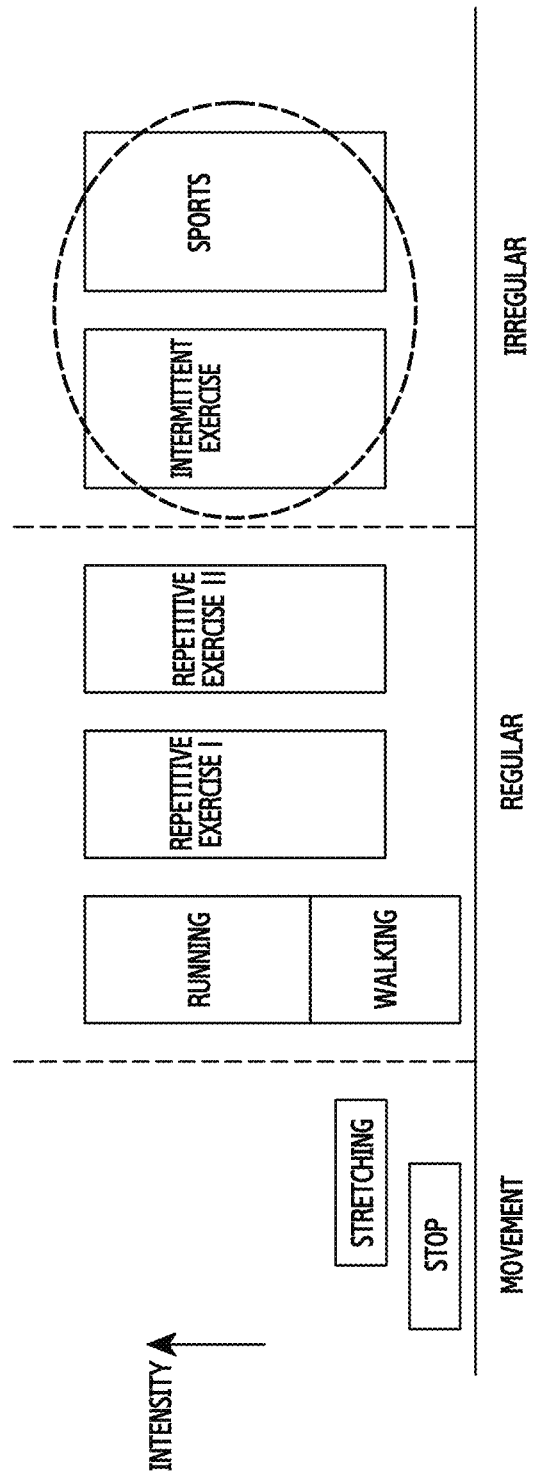
FIG. 10 illustrates an example of distinguishing a user's activity on the basis of sensor data according to one exemplary embodiment.

FIG. 10 illustrates an example of distinguishing a user's activity on the basis of sensor data according to one exemplary embodiment.

Referring to FIG. 10, the first processor 440 may distinguish user movement when standing, such as stop action (e.g. no movement), stretching, or the like on the basis of the sensor data. In addition, the first processor 440 may distinguish a regular exercise or an irregular exercise on the basis of the sensor data. Among regular exercise, the first processor 440 may distinguish whether the user's movement is high intensity (e.g., running, jogging) or low intensity (e.g., walking). For example, a repetitive exercise 1 may be for a user movement in which greater variation is detected, such as when the user is using elliptical or rowing machine, or the like. A repetitive exercise 2 may be for a user movement in which smaller variation and rotation are detected, such as when the user is rope jumping, doing push-ups, or the like.

Among, irregular exercise, the first processor 440 may distinguish intermittent exercise, sports activity, or the like. For example, intermittent exercise may be exercises where user movement is detected irregularly. In addition, sports exercises may indicate user activity during sporting events such as basketball, baseball, soccer, badminton, or the like. The repetitive exercises 1 and 2, the intermittent exercise, and the sports exercise may have higher intensities than walking. Conventionally, although the movement intensity is high, due to its irregular nature, irregular exercise cannot be reliably determined, and thus information regarding irregular exercise (e.g. user's activity exercise) cannot be provided. However, as explained above for example in connection with FIGS. 9A and 9B and below in connection with FIG. 11, the first processor 440 may use the sensor data to determine irregular exercises to be user's activity exercises.

Figure 11:
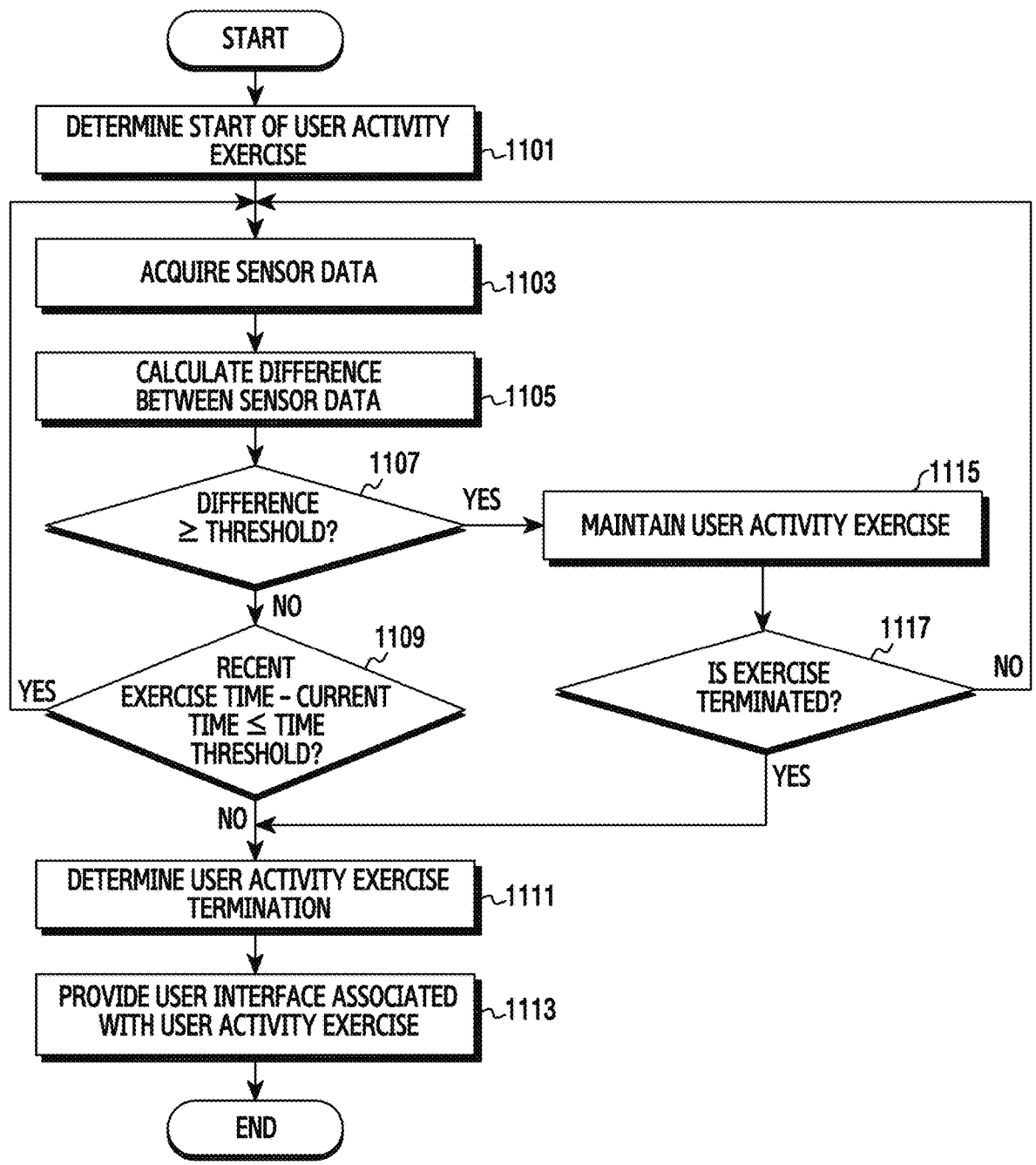
FIG. 11 is a flowchart illustrating a method of determining a user activity exercise according to one exemplary embodiment.

FIG. 11 is a flowchart illustrating a method of determining a user activity exercise according to one exemplary embodiment.

Referring to FIG. 11, in operation 1101, the electronic device 400 (e.g., the first processor 440) may determine a start of a user activity exercise. For example, if change in the difference between two data points in the sensor data is continued for a specific time period and if the period of sensor data is irregular, the first processor 440 may determine a user's movement as the user activity exercise, as shown in FIG. 7. The determined start of the user activity exercise may be used as the start time of the user activity exercise.

In operation 1103, the electronic device 400 (e.g., the first processor 440) may acquire sensor data. Since operation 1103 is similar or identical to operation 501 or operation 701, detailed descriptions thereof may be omitted. The sensor data acquired in operation 1103 may be from different sensors than those used in operation 501 or operation 701. For example, the sensor used in operation 501 or operation 701 may be the acceleration sensor, while the sensor used in operation 1103 may be the gyro sensor, the geomagnetic sensor, and/or the heart rate sensor.

In operation 1105, the electronic device 400 (e.g., the first processor 440) may calculate the difference between two data points in the sensor data. As shown in FIGS. 8 and 9, the difference may be calculated from two points in the current sensor value, the short average value, or the long average value. Since operation 1105 is similar or identical to operation 503 or operation 703, detailed descriptions thereof may be omitted.

In operation 1107, the electronic device 400 (e.g., the first processor 440) may determine whether the difference is greater than or equal to a threshold. The threshold may be preset by the electronic device 400. Alternatively, the threshold may be set by the first processor 440 based on a previous difference.

The first processor 440 may perform operation 1115 if the difference is greater than or equal to the threshold, and may perform operation 1109 if the difference is less than the threshold.

In the case of the user activity exercise, unlike the general exercise, the movement may be irregular, and there may be great changes in the exercise intensity. For example, participating in soccer includes at various times, running, walking, stopping, etc. Therefore conventionally, the system may erroneously determine that the exercise is terminated when the user is temporarily stopped during the game. To avoid this, and to provide an advantage over the prior art, embodiment of the present disclosure uses recent exercise time or the current time to determine whether the user activity exercise is continued.

For example, if the difference is less than the threshold, in operation 1109, the electronic device 400 (e.g., the first processor 440) may subtract the current time from a recent exercise time. The recent exercise time may be the most recent time when the user movement exceeds the threshold. The first processor 440 may then determine whether the resulting time interval is greater than or equal to a time threshold. For example, the time threshold may be set by considering typical break intervals (e.g. when there is little user movement) in various sporting events such as basketball, baseball, soccer, or the like.

The first processor 440 may return to operation 1103 if the resulting time interval is less than or equal to the threshold, and may perform operation 1111 if the resulting time interval exceeds the time threshold.

In operation 1111, the first processor 440 may determine that the user activity exercise is terminated. For example, the first processor 440 may determine that the user activity exercise is terminated if the user has idled for too long and too much time has elapsed from the recent exercise time.

When the user activity exercise is terminated, in operation 1113, the electronic device 400 (e.g., the first processor 440) may deliver user activity information to the second processor 450. The electronic device 400 (e.g., the second processor 450) may provide a user interface for the user activity information at the request of the user. The user interface may be for the general exercise information consisting of at least one of text, image, and video. For example, the user interface may include at least one of an exercise time, an exercise distance, an exercise type, an exercise intensity, and consumed calorie. The first processor 440 or the second processor 450 may calculate consumed calorie by using at least one of the exercise time, the exercise distance, the exercise type, and the exercise intensity.

If the difference is greater than or equal to the threshold, in operation 1115, the electronic device 400 (e.g., the first processor 440) may determine that the user activity exercise is maintained, i.e. the user activity exercise is continuing.

In operation 1117, the electronic device 400 (e.g., the first processor 440) may monitor whether the user activity exercise is terminated. The first processor 440 may store user activity exercise information (e.g. the sensor data) in a memory (e.g., the memory 460) until the user activity exercise is terminated.

The first processor 440 may perform operation 1111 if it is determined that the exercise is terminated, and may return to operation 1103 if it is determined that the exercise is not terminated.

Figure 12:
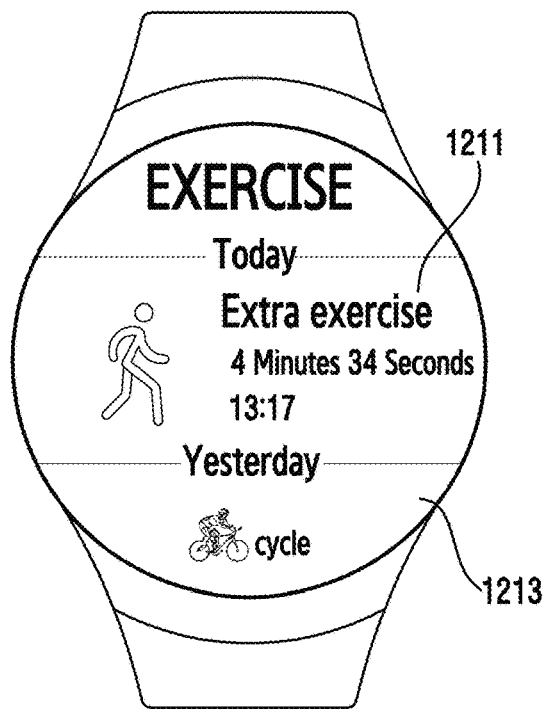
FIG. 12 illustrates examples of user interfaces for user activity exercise according to one exemplary embodiment.
Figure 12:
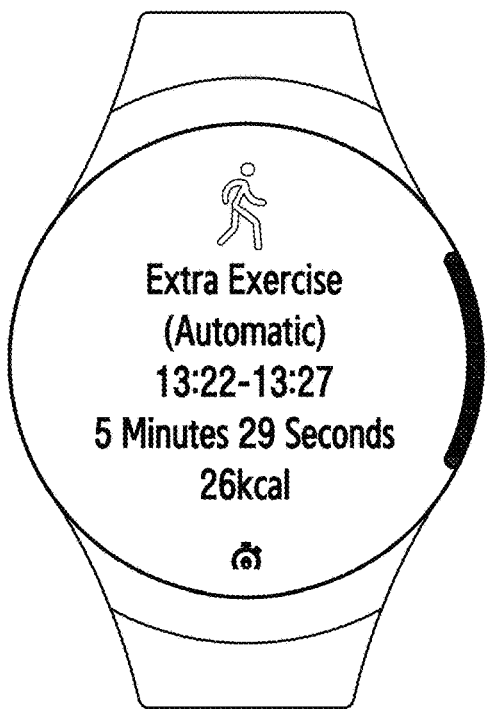
Figure 12:
Figure 12:

FIG. 12 illustrates examples of user interfaces for user activity exercise according to one exemplary embodiment.

Referring to FIG. 12, the electronic device 400 (e.g., the second processor 450) may provide a first user interface 1210 for representing daily exercise information. The first user interface 1210 may include today's exercise information 1211 and yesterday's exercise information 1213. The today's exercise information 1211 is related to user activity information, and may determine extra exercise undertaken by the user, classify the extra exercise, and display an icon corresponding to the extra exercise. The today's exercise information 1211 may further include the exercise duration time (4 minutes 34 seconds), and the exercise start time (13:17). The yesterday's exercise information 1213 may include icon and text (e.g., cycle) corresponding to the exercise type. The electronic device 400 (e.g., the second processor 450) may provide a second user interface 1220 if the user requests to view the user activity information. The second user interface 1220 may show the exercise type (extra exercise), the exercise time (13:22~13:27), the exercise duration time (5 minutes 29 seconds), and consumed calories (26 kcal).

Although the exercise type is indicated as "extra exercise" in FIG. 12, the electronic device 400 (e.g., the second processor 450) may display a specific exercise type depending a user input or external sensing information received from an external electronic device (e.g., a peripheral device equipped in shoes, clothing, bands, or the like). For example, if the user selects the exercise type as "soccer" and selects an exercise start button, the second processor 450 may provide a user interface for representing exercise information by using sensor data acquired until an exercise end button is pressed by the user or until a time at which a user movement is not detected for a specific period of time. In another example, the second processor 450 may classify the exercise type as "soccer" by using the sensor data acquired by the sensor module 410, and may display an icon corresponding to the soccer. Alternatively, the first processor 440 may determine a high-intensity exercise by using the sensor data acquired by the sensor module 410, and may determine the exercise type by further considering the high-intensity exercise and the external sensing information. The second processor 450 may provide a user interface for representing exercise information including the exercise type determined by further considering the external sensing information.

The electronic device 400 (e.g., the second processor 450) may provide a third user interface 1230 for user activity information. The third user interface 1230 may include consumed calories (1587 kcal), high-intensity exercise time (53 minutes), low-intensity exercise time (1 hour 40 minutes), and the exercise date (yesterday). The first processor 440 or the second processor 450 may calculate consumed calories based on the exercise time or the exercise intensity. By using the disclosed embodiments, more accurate exercise time, exercise intensity, and consumed calorie for the user activity exercise may be provided. The electronic device 400 (e.g., the second processor 450) may provide a fourth user interface 1240 for the user activity information. The fourth user interface 1240 may include the exercise duration (4 minutes), consumed calories (19 kcal), the exercise time (13:17 to 13:21), and the exercise date (today).

According to one exemplary embodiment, a method of operating an electronic device including one or more sensor modules may include acquiring sensor data from at least one sensor module among the one or more sensor modules, calculating a difference between at least two data points in the acquired sensor data, determining user's activity information based on at least one of a period of the sensor data, a magnitude of the difference, and a change amount of the difference, and displaying a user interface related to the user's activity information.

The determining may include determining whether the period of the sensor data is regular if the difference is greater than or equal to a first threshold.

The determining may include determining the user's activity information as a user activity exercise if the difference is greater than or equal to a first threshold, if the period of the sensor data is irregular, and if the change amount of the difference is greater than a second threshold.

The determining may include determining the user's activity information as a general exercise if the difference is greater than or equal to a first threshold and if the period of the sensor data is regular.

The determining may include determining the user's activity information as a daily-life movement if the difference is less than or equal to a first threshold.

The operating method may further include determining whether a user activity exercise is maintained based on an interval between a recent exercise time and a current time, if the user's activity information is the user activity exercise.

The operating method may further include determining an exercise intensity based on the change amount of the difference during a specific period of time, and providing information related to the exercise intensity.

The operating method may further include acquiring sensor data from another sensor module different from the at least one sensor module if the period of the sensor data is regular and if the difference is greater than or equal to a first threshold, and determining an exercise type for the user's activity information based on the sensor data from the other sensor module.

According to one exemplary embodiment, a computer readable recording medium may include a program for performing operations of acquiring sensor data from at least one sensor module among the one or more sensor modules, calculating a difference between at least two data points in the acquired sensor data, determining user's activity information based on at least one of a period of the sensor data, a magnitude of the difference, and a change amount of the difference, and displaying a user interface related to the user's activity information.

The computer readable recording medium may include a hard disk, a floppy disk, a magnetic medium (e.g., a magnetic tape), an optical storage medium (e.g., a Compact Disc-ROM (CD-ROM) or a Digital Versatile Disc (DVD), a magnetic-optic medium such as a floptical disc), an internal memory, or the like. The instruction may include a code created by a compiler or a code executable by an interpreter. The module or programming module according to various exemplary embodiments may further include at least one or more constitutional elements among the aforementioned constitutional elements, or may omit some of them, or may further include other constitutional elements. Operations performed by a module, programming module, or other constitutional elements according to various exemplary embodiments may be executed in a sequential, parallel, repetitive, or heuristic manner. Alternatively, at least some of the operations may be executed in a different order or may be omitted, or other operations may be added.

Aspects of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

Various exemplary embodiments of the present disclosure disclosed in the specification and the drawing are merely a specific example presented for clarity and are not intended to limit the scope of the present disclosure. Therefore, in addition to the embodiments disclosed herein, various changes in forms and details made without departing from the technical concept of the present disclosure will be construed as being included in the scope of the present disclosure.

What is claimed is:

1. An electronic device comprising:
   one or more sensor modules;
   at least one memory;
   a display; and
   a first processor,
   wherein the first processor is operatively coupled to the one or more sensor modules, the at least one memory, and/or the display,
   wherein the first processor is configured to:
      acquire sensor data from a first sensor module among the one or more sensor modules,
      calculate a difference between at least two data points in the acquired sensor data,
      determine user's activity information based on at least one of a period of the acquired sensor data, a magnitude of the difference, and a change amount of the difference,
      if the period of the acquired sensor data is regular and if the magnitude of the difference is greater than or equal to a first threshold, drive a second sensor module different from the first sensor module based on the acquired sensor data, and
      display, on the display, a user interface related to the user's activity information.

2. The electronic device of claim 1, wherein the first processor is further configured to determine whether the period of the acquired sensor data is regular if the magnitude of the difference is greater than or equal to the first threshold.

3. The electronic device of claim 1, wherein the first processor is further configured to determine the user's activity information as a user activity exercise if:
   the magnitude of the difference is greater than or equal to the first threshold,
   the period of the acquired sensor data is irregular, and
   the change amount of the difference is greater than a second threshold.

4. The electronic device of claim 1, wherein the first processor is further configured to determine the user's activity information as a general exercise if the magnitude of the difference is greater than or equal to the first threshold and if the period of the acquired sensor data is regular.

5. The electronic device of claim 1, wherein the first processor is further configured to determine the user's activity information as a daily-life movement if the magnitude of the difference is less than or equal to the first threshold.

6. The electronic device of claim 1, wherein the first processor is further configured to determine, if the user's activity information is a user activity exercise, whether the user activity exercise is maintained based on an interval between a recent exercise time and a current time.

7. The electronic device of claim 1,
   wherein the first processor is further configured to determine an exercise intensity based on the change amount of the difference during a specific period of time, and
   wherein a second processor is configured to display information related to the exercise intensity.

8. The electronic device of claim 1, wherein the first processor is further configured to determine an exercise type for the user's activity information based on the acquired sensor data from the second sensor module.

9. The electronic device of claim 1, wherein the electronic device is an electronic device wearable on a user's body.

10. The electronic device of claim 1,
    wherein the first processor is always in an active state, and
    wherein a second processor is configured to selectively switch between the active state and an inactive state.

11. The electronic device of claim 1, wherein the at least one memory is integrated with the first processor or is located outside the first processor.

12. The electronic device of claim 1, wherein the first processor is further configured to:
    receive external sensing information from an external electronic device, and
    determine the user's activity information using the external sensing information.

13. A method of operating an electronic device including one or more sensor modules, the method comprising:
    acquiring sensor data from a first sensor module among the one or more sensor modules;

calculating a difference between at least two data points in the acquired sensor data;

determining user's activity information based on at least one of a period of the acquired sensor data, a magnitude of the difference, and a change amount of the difference;

if the period of the acquired sensor data is regular and if the magnitude of the difference is greater than or equal to a first threshold, driving a second sensor module different from the first sensor module based on the acquired sensor data; and displaying a user interface related to the user's activity information.

14. The method of claim 13, wherein the determining further comprises determining whether the period of the acquired sensor data is regular if the magnitude of the difference is greater than or equal to the first threshold.

15. The method of claim 13, wherein the determining further comprises determining the user's activity information as a user activity exercise if:

the magnitude of the difference is greater than or equal to the first threshold, the period of the acquired sensor data is irregular, and the change amount of the difference is greater than a second threshold.

16. The method of claim 13, wherein the determining further comprises determining the user's activity information as a general exercise if the magnitude of the difference is greater than or equal to the first threshold and if the period of the acquired sensor data is regular.

17. The method of claim 13, wherein the determining further comprises determining the user's activity information as a daily-life movement if the magnitude of the difference is less than or equal to the first threshold.

18. The method of claim 13, if the user's activity information is a user activity exercise, further comprising determining whether the user activity exercise is maintained based on an interval between a recent exercise time and a current time.

19. The method of claim 13, further comprising:

driving a second sensor module different from the first sensor module based on the acquired sensor data if the period of the acquired sensor data is regular and if the magnitude of the difference is greater than or equal to the first threshold; and determining an exercise type for the user's activity information based on the acquired sensor data from the second sensor module.

* * * * *